US006673756B2

(12) United States Patent
Sonnenberg et al.

(10) Patent No.: US 6,673,756 B2
(45) Date of Patent: Jan. 6, 2004

(54) MULTIPHASE SOAPS

(75) Inventors: Steffen Sonnenberg, Holzminden (DE); Marcus Ohrmann, Heinade (DE); Theodor Schmidt, Höxter (DE); Rolf-Günter Schmidt, Holzminden (DE)

(73) Assignee: Symrise GmbH & Co. KG (DE)

( * ) Notice: Subject to any disclaimer, the term of this patent is extended or adjusted under 35 U.S.C. 154(b) by 80 days.

(21) Appl. No.: 10/068,708

(22) Filed: Feb. 6, 2002

(65) Prior Publication Data

US 2002/0173436 A1 Nov. 21, 2002

Related U.S. Application Data

(63) Continuation-in-part of application No. 09/782,694, filed on Feb. 13, 2001, now abandoned.

(51) Int. Cl.$^7$ .................................................. A61K 7/50

(52) U.S. Cl. ....................... 510/141; 510/146; 510/147; 510/447; 264/75

(58) Field of Search ................................ 510/141, 146, 510/147, 447; 264/75

(56) References Cited

U.S. PATENT DOCUMENTS

| | | | |
|---|---|---|---|
| 4,036,775 A | 7/1977 | Trautvetter et al. | 252/134 |
| 4,435,310 A | 3/1984 | Lowry | 252/370 |
| 5,198,140 A | 3/1993 | Joshi et al. | 252/90 |
| 5,217,639 A | 6/1993 | Mottola | 252/90 |

FOREIGN PATENT DOCUMENTS

| | | |
|---|---|---|
| CA | 2001717 | 4/1990 |
| DE | 1 924 980 | 11/1970 |
| DE | 1 953 916 | 5/1971 |
| DE | 24 55 982 | 8/1976 |
| DE | 31 45 813 | 6/1983 |
| EP | 0 594 077 | 2/1996 |
| JP | 62048799 | 3/1987 |
| JP | 1247499 | 10/1989 |

OTHER PUBLICATIONS

Soap and Detergents, Louis Spitz (date unavailable) 0–935315–72–1 pp. 172–206.

D. Asteroth, Production of Soap (date unavailable) p. 76, 3–921956–55–2, Cutting Machines.

*Primary Examiner*—Necholus Ogden
(74) *Attorney, Agent, or Firm*—Pendorf & Cutliff

(57) ABSTRACT

Multiphase soaps in which the individual phases are highly visible when viewed from above and from the side have high stability. Their use permits various scent experiences to be achieved during the washing operation.

7 Claims, 12 Drawing Sheets

MULTIPHASE SOAPS

This application is a Continuation In-Part of U.S. Ser. No. 09/782,694, filed Feb. 13, 2001 now abandoned.

FIELD OF THE INVENTION

The invention relates to multiphase soaps in which the individual phases are highly visible when viewed from above and from the side, to their preparation and to their use for the application of different scent experiences during the washing operation.

BACKGROUND OF THE INVENTION

DE-A 31 45 813 describes the preparation and use of picture and changing motif soaps. The preparation takes place by stamping various horizontal soap layers which have been prepared by means of an extruder. This process cannot be operated efficiently, meaning that use of these soaps is not possible in the mass consumer market. A particular disadvantage of this type of horizontally cut soap is the fact that the different horizontal soap layers cannot be distinguished or can be distinguished only with great difficulty by the consumer when viewed from a customary viewing angle of about 45° and above. This effect intensifies with increasing use time since the two phases become thinner as a result of being washed off.

This disadvantage also applies to the diverse horizontally cut soaps described in EP-A 0 366 209 and U.S. Pat. No. 5,198,140. U.S. Pat. No. 5,198,140 describes the preparation of an interlocked soap having increased strength. EP-A 0 366 209 describes the preparation of horizontal multiphase soaps by a casting process. However, casting processes are only suitable for the preparation of small numbers of bars, but not for the production of soaps for the mass consumer market.

EP-A 0 594 077 describes the preparation of spiral-shaped multiphase soaps which are prepared using a special compression head following radial rotation of the soap strand. Particularly in cases where different soap bases are used, the stability of the type of soap is limited in its application by the many phase boundaries.

DE-A 1 924 980 describes a process for the preparation of a multiphase soap with one or more sheaths which surround a core. This type of soap cannot be differentiated visually by the consumer from a normal single-phase soap before use and also in between during use, as a result of which there is no applications-related advantage.

The same also applies to soaps prepared in accordance with JP-A 62/48799. Here, a multilayer round strand is produced.

Soaps are also known in which a vertical cut in the transverse or in the longitudinal direction of the soap separates the two soap phases (e.g., JP 1-247499). In this type of soap, both phases are visible at the same time. However, the vertical type of soap, during use by the consumer and during continuous storage, exhibits the decisive disadvantage of lower stability of the overall bar of soap. Because of the small and straight contact areas, a vertically cut soap may break even as a result of the soap simply falling to the ground. In particular, when different soap formulations are used for the individual parts of the soap, shrinkage and drying out can lead to breaking of the soap. Also, when different soap formulations are used, the strength of the diagonally cut soap, in contrast to vertically joined soap, is ensured during use by the consumer over the entire use period. As a result, it may, in the future, also be possible to combine less expensive soap formulations with more expensive soap formulations, or to combine different soap formulations, which are incompatible with one another because of shrinkage, for the preparation.

EP-A 0 545 716 describes the preparation of a multidimensionally curved two-phase soap. By using the casting process, a two-phase soap is produced, which is not suitable for the mass consumer market due to the costly preparation. Since the soap here is a cast soap in which no pressure is subsequently exerted in the form of stamping, the durability of this type of soap is limited during daily use.

Marbled soaps are also known (DE-A 2 455 982, DE 2 431 048, U.S. Pat. No. 1,587,430 and DT 1 953 916). Here, differently colored soap phases are mixed intensively with one another using special pressing cylinders or screw presses, such that a marbled effect arises. Furthermore, the color can also be injected into the soap stream during the preparation of the soap. The soaps here consist of one phase.

A further multicolored single-phase soap is described in U.S. Pat. No. 4,435,310. Here, by injecting color during the preparation of the soap strands and by manually turning the extruder head, a multicolored sinusoidal soap is obtained from one cake.

SUMMARY OF THE INVENTION

The objects of the present invention were multiphase soaps in which the different phases may have different ingredients which, during use, have a stability comparable with that of a single-phase soap. In particular, it is possible for the different phases to comprise different perfume oils so that, during use, different successive scent experiences are possible.

We have found multiphase soaps comprising two or more phases which are characterized in that the latter are highly visible when viewed from above and from the side.

The multiphase soaps according to the present invention exhibit superproportional strength, which virtually corresponds with the stability of a single-phase soap.

DETAILED DESCRIPTION OF THE INVENTION

Figure 1A:
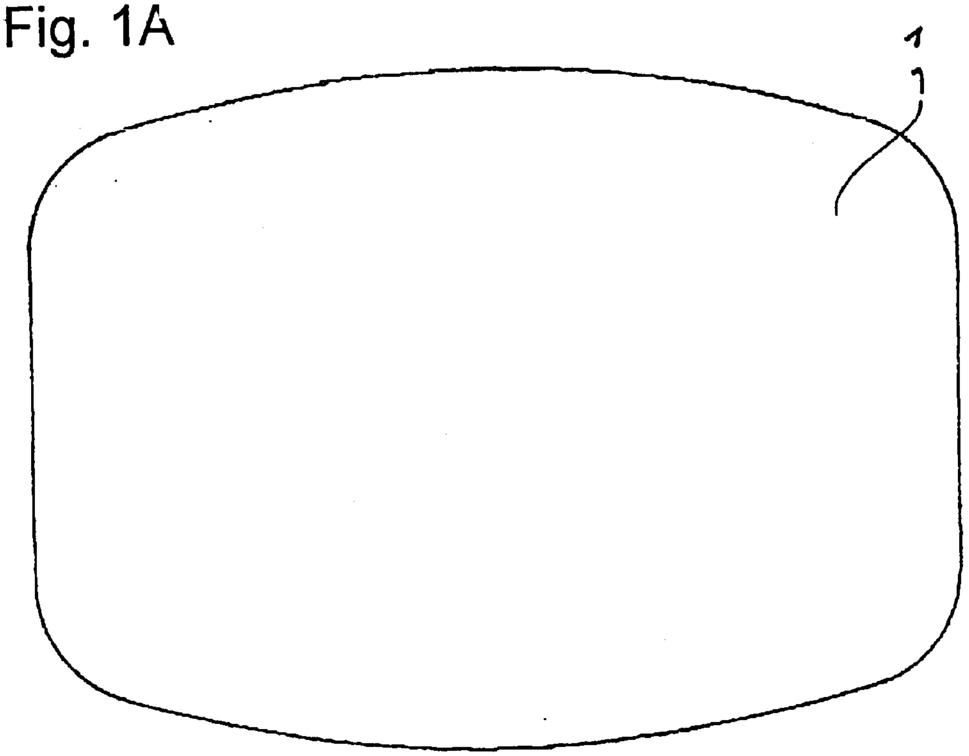
FIG. 1A shows a top view of a single-phase standard soap.

Multiphase soaps are preferred in which each phase is visible in the vertical, longitudinal and transverse projection to at least 15%, based on the overall projected area.

Even more preferred are multiphase soaps in which each phase is visible in the vertical, longitudinal and transverse projection to at least 20%, based on the overall projected area.

In a preferred embodiment of the multiphase soaps according to the present invention, adjacent phase areas are cut diagonally and cambered towards one another. The cambering is achieved during the preparation using pressure. Multiphase soaps with cambered points of intersection have particular stability.

The multiphase soaps according to the present invention preferably comprise two phases which have a different composition.

In general, the multiphase soaps according to the invention can be used for all washing purposes, in particular for washing purposes where an application of more than one ingredient is desired. The application can here take place simultaneously or successively in a targeted manner.

In particular, it is advantageous that each phase of the multiphase soap can be tailored for the respective preferred application. By the composition of the soap base and optionally further additives or fillers, it is possible to fashion the respective soap phase as a medium which is best for the application concerned. Thus, by means of pH, ionic strength, water content, fat content, fat composition and similar parameters, for example, it is possible to optimize the conditions for ingredients.

The multiphase soaps according to the invention can be used, for example, for the washing or cleaning of skin, hair, textile, plastic, metal, wood, ceramic, glass, composites and the like.

The soap bases for the multiphase soaps according to the present invention are known per se (Soaps and Detergents, Luis Spitz, 0-935315-72-1 and Production of Soap, D. Osteroth, 3-921956-55-2). For example, soap bases such as alkali metal soaps consisting of animal and/or vegetable substances, syndets consisting of synthetic surfactants or combinations of the two may be used for the multiphase soaps according to the present invention.

Preference is given to the use of natural vegetable soap raw materials, such as, for example, glycerol, castor oil, coconut oil, olive oil, palm oil, palm kernel oil, peanut oil, almond oil, ricinus oil, cocoa butter, poppy oil, maize oil, hemp oil, soybean oil, rapeseed oil, cottonseed oil and sunflower oil.

Preference is given to the use of natural animal soap raw materials such as, for example, pork fat, beef tallow, sheep tallow or fish oil.

Said oils and fats consist of triglycerides of straight-chain saturated, mono- and polyunsaturated acid having six to thirty carbon atoms. From these soap raw materials, preference is given to preparing the sodium and the potassium soaps by saponification.

Preference is given to the use of synthetic soap raw materials, such as, for example, alkyl sulphoacetates, sulphosuccinates, monoglyceride sulphates, acyl isethionates, glyceryl ether sulphonates, alkylsulphonates, ether sulphonates, acylsulphonates or alkylacyl sulphonates.

It is also possible to use agents for setting a pH or the ionic strength. Examples which may be mentioned are sodium carbonate, sodium hydroxide, phosphoric acid and salts thereof, sodium acetate, acetic acid, citric acid and salts thereof, sodium hydrogencarbonate, triethanolamine, EDTA, disodium-EDTA, tetrasodium-EDTA.

The person skilled in the art is of course aware that cosmetic preparations are in most cases inconceivable without customary auxiliaries and additives. These include, for example, bodying agents, fillers, perfume, dyes, emulsifiers, additional active ingredients, such as vitamins or proteins, light protection agents, stabilizers, insect repellants, alcohol, water, salts, and antimicrobially, proteolytically or keratolytically effective substances.

The soap base can comprise, as further ingredients, for example, perfume oils, cosmetic ingredients, dyes and further additives.

Ingredients which may be present in the multiphase soaps according to the invention can have additional effects. Examples which may be mentioned are: preservatives, abrasives, anti-acne agents, agents against skin ageing, antibacterial agents, anticellulite agents, antidandruff agents, anti-inflammatory agents, irritation-preventing agents, irritation-suppressing agents, antimicrobial agents, antioxidants, astringents, perspiration-suppressing agents, antiseptics, antistatics, binders, buffers, carrier materials, chelating agents, cell stimulants, cleansing agents, care agents, hair-removal agents, surface-active substances, deodorizing agents, antiperspirants, softeners, emulsifiers, enzymes, essential oils, fibres, film formers, fixatives, foam formers, foam stabilizers, antifoams, foam boosters, fungicides, gelling agents, gel-forming agents, haircare agents, hair-shaping agents, hair-smoothing agents, moisture-donating agents, moisturizing substances, humectant substances, bleaching agents, strengthening agents, stain-removal agents, optical brighteners, impregnating agents, soil repellants, friction-reducing agents, lubricants, moisturizing creams, ointments, opacifiers, plasticizing agents, covering agents, polish, sheen agents, polymers, powders, proteins, refatting agents, abrasive agents, silicones, skin-calming agents, skin-cleansing agents, skin care agents, skin-healing agents, skin-lightening agents, skin-protecting agents, skin-softening agents, cooling agents, skin-cooling agents, warming agents, skin-warming agents, stabilizers, UV-absorbing agents, UV filters, washing agents, softeners, suspending agents, skin-tanning agents, thickeners, vitamins, oils, waxes, fats, phospholipids, saturated fatty acids, mono- or polyunsaturated fatty acids, -hydroxy acids, polyhydroxy fatty acids, liquefying agents, dyes, colour-protection agents, pigments, anti-corrosives, aromas, flavours, fragrances or other customary constituents of a cosmetic or dermatological formulation, such as alcohols, polyols, electrolytes, organic solvents or silicone derivatives.

It is preferred to add different perfume oils which are released successively and, during the washing operation, convey different, successive scent experiences to the user, or, as a result of the simultaneous release of the individual perfume oils, form a new more intensive scent.

Examples of fragrances in the perfume oils for the multiphase soaps according to the present invention are given, for example, in S. Arctander, Perfume and Flavor Materials, Vol. I and II, Montclair, N. J., 1969, published privately or K. Bauer, D. Garbe and H. Surburg, Common Fragrance and Flavor Materials, $3^{rd}$. Ed., Wiley-VCH, Weinheim 1997.

Individual examples which may be mentioned are: Extracts from natural raw materials such as essential oils, concretes, absolutes, resins, resinoids, balsams, tinctures, such as, for example, ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; corianda oil; costus root oil; cumin oil; cypress oil; Davana oil; dill herb oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; camomile blue oil; camomile Roman oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lavage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary sage oil; nutmeg oil; myrrh absolute; myrrh oil; myrtenol; clove leaf oil; clove flower oil; neroli oil; olibanum absolute; olibanum oil; opopanax oil; orange-flower absolute; orange oil; origanum oil; palmarosa oil; patchouli oil; perilla oil; peruvian balsam oil; parsley leaf oil; parsley seed oil; petitgrain oil; peppermint oil; pepper oil; pimenta oil; pine oil; pennyroyal oil; rose absolute; rosewood oil; rose oil; rosemary oil; dalmation sage oil; Spanish sage oil; sandalwood oil; celery seed oil; spike lavender oil; Japanese anise oil; styrax oil; tagetes oil; fir needle oil; tea-tree oil; turpentine oil; thyme oil; Tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof, or ingredients isolated therefrom;

individual fragrances from the group of hydrocarbons, such as, for example, 3-carene; α-pinene; β-pinene; α-terpinene; γ-terpinene; p-cymene; bisabolene; camphene; caryophyllene; cedrene; farnesene; limonene; longifolene; myrcene; ocimene; valencene; (E,Z)-1,3,5-undecatriene;

of aliphatic alcohols, such as, for example, hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-¾-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; of aliphatic aldehydes and 1,4-dioxacycloalken-2-ones thereof, such as, for example, hexanal; heptanal; octanal; nonanal; decanal; undecanal; dodecanal; tridecanal; 2-methyl-octanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde; of aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; of aliphatic sulphur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles, such as, for example, 2-nonenenitrile; 2-tridecene-nitrile; 2,12-tridecenenitrile; 3,7-dimethyl-2,6-octadienenitrile; 3,7-dimethyl-6-octenenitrile;

of aliphatic carboxylic acids and esters thereof, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate, isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl 2-isoamyloxyacetate; methyl 3,7-dimethyl-2,6-octadienoate;

of acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof; of acyclic terpene aldehydes and ketones, such as, for example, geranial; neral; cirtonellal; 7-hydroxy-3,7-dimethyloctanal; 7-methoxy-3,7-dimethyl-octanal; 2,6,10-trimethyl-9-undecenal; geranylacetone; and the dimethyl and diethyl acetals of geranial, neral, 7-hydroxy-3,7-dimethyloctanal;

of cyclic terpene alcohols, such as, for example, menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates, 3-methyl-2-butenoates thereof;

of cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-iron; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methano-naphthalen-8(5H)-one; nootkatone; dihydronootkatone; alpha-sinensal; beta-sinensal; acetylated cedarwood oil (methyl cedryl ketone);

of cyclic alcohols, such as, for example, 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols, such as, for example, alpha-3,3-trimethyl-cyclo-hexylmethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of cyclic and cycloaliphatic ethers, such as, for example, cineol; cedryl methyl ether; cyclododecyl methyl ether; (ethoxymethoxy)cyclododecane; alpha-cedrene epoxide; 3a,6,6,9a-tetramethyldodecahydronaphtho[2, 1-b]furan; 3a-ethyl-6,6,9a-trimethyidodecahydronaphtho[2, 1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic ketones, such as, for example, 4-tert-butylcyclohexanone; 2,2,5-trimethyl-5-pentylcyclopentanone; 2-heptylcyclopentanone; 2-pentylcyclo-pentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclo-hexanone; 4-tert-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

of cycloaliphatic aldehydes, such as, for example, 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of cycloaliphatic ketones, such as, for example, 1-(3,3-dimethylcyclo-hexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl 2,4-dimethyl-3-cyclohexen-1-yl ketone;

of esters of cyclic alcohols such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetra-hydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

of esters of cycloaliphatic carboxylic acids, such as, for example, allyl 3-cyclohexyl-propionate; allyl cyclohexyloxyacetate; methyl dihydrojasmonate; methyl jasmonate; methyl 2-hexyl-3-oxocyclopen-tanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolan-2-acetate;

of aromatic hydrocarbons, such as, for example, styrene and diphenylmethane;

of araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenyl-pentanol; 3-methyl-5-phenylpentanol; 3-phenyl-2-propen-1-ol; 4-methoxybenzyl alcohol; 1-(4-isopropylphenyl)ethanol;

of esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; of araliphatic ethers, such as, for example, 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethylindeno[1,2-d]-m-dioxin;

of aromatic and araliphatic aldehydes, such as, for example, benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4methoxy-benzaldehyde; 4-hydroxy-3-methoxybenzaldehyde; 4-hydroxy-3-ethoxy-benzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

of aromatic and araliphatic ketones, such as, for example, acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

of aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

of nitrogen-containing aromatic compounds, such as, for example, 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenenitrile; 5-phenyl-3-methylpentanenitrile; methyl anthranilate; methyl N-methylanthranilate; Schiff bases of methyl anthranilate with 7-hydroxy-3,7-dimethyloctanal; 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

of phenols, phenyl ethers and phenyl esters, such as, for example, estragole; anethole; eugenole; eugenyl methyl ether; isoeugenole; isoeugenyl methyl ether; thymole; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

of heterocyclic compounds, such as, for example, 2,5-dimethyl-4-hydroxy-2H-furan-3-one; 2-ethyl4-hydroxy-5-methyl-2H-furan-3-one; 3-hydroxy-2-methyl-4H-pyran-4-one; 2-ethyl-3-hydroxy-4H-pyran-4-one;

of lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The perfume oils are generally added to the soap base in an amount of from 0.05 to 5% by weight, preferably from 0.1 to 2.5% by weight, more preferably from 0.2 to 1.5% by weight, based on the soap base.

The perfume oils may be added in liquid form, neat or diluted with a solvent for perfuming the soap base. Suitable solvents for this purpose are, for example, ethanol, isopropanol, diethylene glycol monoethyl ether, glycerol, propylene glycol, 1,2-butylene glycol, dipropylene glycol, diethyl phthalate, triethyl citrate, isopropyl myristate, and etc.

In addition, the perfume oils for the multiphase soaps according to the present invention can be adsorbed on a carrier which serves both to distribute the fragrances finely within the product and to release them in a controlled manner during use. Such carriers can be porous inorganic materials, such as light sulphate, silica gels, zeolites, gypsums, clays, clay granules, gas concrete, etc. or organic materials such as woods and cellulose-based substances.

The perfume oils for the multiphase soaps according to the present invention can also be microencapsulated, spray dried, in the form of inclusion complexes or in the form of extrusion products and be added in this form to the soap base to be perfumed.

The properties of the perfume oils modified in this way can optionally be further optimized by so-called "coating" with suitable materials with regard to a more targeted fragrance release, for which purpose preference is given to using wax-like polymers such as, for example, polyvinyl alcohol.

The microencapsulation of the perfume oils can, for example, be carried out by the so-called coacervation method using capsule materials made from, for example, polyurethane-like substances or soft gelatins. The spray-dried perfume oils can, for example, be prepared by spray drying an emulsion or dispersion comprising the perfume oil, where the carriers used can be modified starches, proteins, dextrin and vegetable gums. Inclusion complexes can be prepared, for example, by introducing dispersions of the perfume oil and cyclodextrins or urea derivatives into a suitable solvent, e.g., water. Extrusion products can be obtained by melting the perfume oils with a suitable wax-like substance and by extrusion with subsequent solidification, optionally in a suitable solvent, e.g., isopropanol.

The perfume oils may be released simultaneously or successively during use. In particular, perfume oils are used which are released successively as a result of the targeted application of the individual soap phases.

The fragrances can also be used in the form of precursors.

Non-limiting examples of fragrance precursors with which the multiphase soap according to the invention can advantageously be combined are given below:

Acetals releasing alcohols, preferably fragrance alcohols and aldehyde or ketone; ortho esters and ortho carbonates releasing alcohols, preferably fragrance alcohols; esters or carbonates releasing alcohols, preferably fragrance alcohols and sometimes aldehyde or ketone; β-keto esters releasing alcohol, preferably fragrance alcohol and sometimes ketone; hydroxy esters releasing alcohol, preferably fragrance alcohol and lactone; protective hydroxy esters releasing alcohol, preferably fragrance alcohol and lactone and sometimes ketone; arylacrylic esters releasing alcohol, preferably fragrance alcohol or aldehyde, preferably fragrance aldehyde or ketone, preferably fragrance ketone and benzopyranone; β,γ-unsaturated δ-keto esters releasing alcohol, preferably fragrance alcohol; α-amides releasing carboxylic acids; β-amino esters releasing alcohol, preferably fragrance alcohol; organosiloxanes releasing alcohol, preferably fragrance alcohol or aldehyde, preferably fragrance aldehyde or ketone, preferably fragrance ketone; iminoalkylpolysiloxanes releasing aldehyde, preferably fragrance aldehyde or ketone, preferably fragrance ketone; oxazolidones releasing aldehyde, preferably fragrance aldehyde or ketone, preferably fragrance ketone; tartaric acid dioxalanes releasing aldehyde or ketone, preferably citral; oxime carboxylic acids releasing oxime or aldehyde or ketone and alcohol or lactone; α-alkoxy aryl ketone releasing ketone, preferably aryl ketone; 2-benzoylbenzoic esters, 2-alkanoylbenzoic esters and α-keto esters releasing alcohol, preferably fragrance alcohol and/or ketone, preferably fragrance ketone; polymer-bonded imines releasing aldehyde and ketone; serine carbonates releasing alcohol, preferably fragrance alcohol or aldehyde, preferably fragrance aldehyde or ketone, preferably fragrance ketone; dioxolanones releasing aldehyde, preferably fragrance aldehyde or ketone, preferably fragrance ketone and hydroxycarboxylic acid; silicic esters releasing alcohol, preferably fragrance alcohol; cyclic hydroxy esters or cyclic keto esters releasing alcohol, preferably fragrance alcohol, S-glycosides releasing thiol; disulphides releasing thiol; cyclic aldehyde trimers releasing fragrance aldehyde; α-alkoxy-α-alkylidenealdehydes releasing alcohol, preferably fragrance alcohol; esters releasing alcohol, preferably fragrance alcohol, and having additional amide functionality; betaine esters releasing alcohols, preferably fragrance alcohols.

The multiphase soaps according to the invention can comprise plant parts and plant extracts. Examples which may be mentioned are arnica, aloe, beard lichen, ivy, stinging nettle, ginseng, henna, camomile, marigold, rosemary, sage, horsetail or thyme. Animal extracts, such as, for example, royal jelly, propolis, proteins or thyme extracts.

Furthermore, cosmetic oils which can be applied dermally can be incorporated into the multiphase soaps, such as, for example, neutral oils of the Miglyol 812 type, apricot kernel oil, avocado oil, babussu oil, cottonseed oil, borage oil, thistle oil, peanut oil, gamma-oryzanol, rosehip kernel oil, hemp oil, hazelnut oil, currant seed oil, jojoba oil, cherry stone oil, salmon oil, linseed oil, maize germ oil, macadamia nut oil, almond oil, evening primrose oil, mink oil, olive oil, pecan nut oil, peach kernel oil, pistachio kernel oil, rapeseed oil, rice germ oil, ricinus oil, safflower oil, sesame oil, soybean oil, sunflower oil, tea tree oil, rapeseed oil or wheatgerm oil.

The multiphase soaps can comprise UV absorbers (UV filters), such as, for example, Neo Heliopane® to protect against discoloration of the soap or protect against solar irradiation on the skin.

Suitable light protection agents are, for example, organic UV absorbers from the class of 4-aminobenzoic acid and derivatives, salicylic acid derivatives, benzophenone derivatives, dibenzoylmethane derivatives, diphenyl acrylates, 3-imidazol-4-ylacrylic acid and esters thereof, benzofuran derivatives, benzylidene malonate derivatives, polymeric UV absorbers, comprising one or more organosilicone radical, cinnamic acid derivatives, camphor derivatives, trianilino-s-triazine derivatives, 2-hydroxyphenylbenzotriazole derivatives, 2-phenylbenzimidazole-5-sulphonic acid and salts thereof, methyl anthranilate, benzotriazole derivatives.

The UV absorbers given below which can be used for the purposes of the present invention are not of course intended to be limiting.

4-aminobenzoic acid, ethyl 4-aminobenzoate, 2-ethylhexyl 4-dimethylaminobenzoate, glycerol 4-aminobenzoate, homomenthyl salicylate (homosalate), 2-ethylhexyl salicylate, triethanolamine salicylate, 4-isopropylbenzyl salicylate, menthyl anthranilate, ethyl diisopropylcinnamate, 2-ethylhexyl p-methoxycinnamate, methyl diisopropylcinnamate, isoamyl p-methoxycinnamate, p-methoxycinnamic acid diethanolamine salt, isopropyhl p-methoxycinnamate, 2-ethylhexyl 2-cyano-3,3-diphenylacrylate, ethyl 2-cyano-3,3'-diphenylacrylate, 2-phenylbenzimidazole-5-sulphonic acid and salts thereof, 3-(4'-trimethylammonium)-benzylidene-bornan-2-one methylsulphate, terephthalylidene-dibornanesulphonic acid and salts, 4-t-butyl-4'-methoxydibenzoylmethane, β-imidazole-4(5)-acrylic acid (urocaninic acid), 2-hydroxy-4-methoxybenzophenone, 2-hydroxy-4-methoxybenzophenone-5-sulphonic acid, dihydroxy-4-methoxybenzophenone, 2,4-dihydroxybenzophenone, tetrahydroxybenzophenone, 2,2'-dihydroxy-4,4'-dimethoxybenzophenone, 2-hydroxy-4-n-octoxybenzophenone, 2-hydroxy-4-methoxy-4'-methylbenzophenone, 3-(4'-sulpho)benzylidene-bornan-2-one and salts thereof, 3-(4'-methylbenzylidene)camphor, 3-benzylidenecamphor, 3,3'-(1,4-phenylenedimethine)-bis-(7,7-dimethyl-2-oxo-bicyclo-[2.2.1]heptane-1-methanesulphonic acid and salts thereof, 4-isopropyidibenzoylmethane, 2,4,6-trianilino-(p-carbo-2'-ethylhexyl-1 '-oxy)-1,3,5-triazine, phenylene-1,4-bis-(2-benzimidazyl)-3,3'-5,5'-tetrasulphonic acid and salts thereof, particularly the corresponding sodium, potassium or triethanolammonium salts, in particular the disodium salt, 2,2'-(1,4-phenylene)-bis-(1 H-benzimidazole-4,6-disulphonic acid), monosodium salt, N-[(2 and 4)-[2-(oxoborn-3-ylidene)methyl]benzyl]acrylamide polymer, phenol, 2-(2H-benzotriazol-2-yl)-4-methyl-6-(2-methyl-3-(1,3,3,3-tetramethyl-1-(trimethylsilyl)-oxy)-disiloxyanyl)-propyl, 4,4'-[(6-[4-(1,1-dimethyl)aminocarbonyl)-phenylamino]-1,3,5-triazine-2,4-diyl)diimino]-bis-(benzoate-2-ethylhexylester), 2,2'-methylene-bis-(6-(2H-benzotriazol-2-yl)-4-1,1,3,3-tetramethylbutyl)-phenol), 2,4-bis-[4-(2-ethylhexyloxy)-2-hydroxy-phenyl]-1,3,5-triazine, benzylidenemalonate-polysiloxane, glyceryl ethyl hexanoate dimethoxycinnamate, disodium 2,2'-dihydroxy-4,4'-dimethoxy-5,5'-disulphobenzophenone, dipropylene glycol salicylate, sodium hydroxy-methoxybenzophenone-sulphonate, tris(2-ethylhexyl) 4,4',4-(1,3,5-triazine-2,4,6-triyltriimino)-tris-benzoate, 2,4-bis-[{(4-(2-ethyl-hexyloxy)-2-hydroxy}-phenyl]-6-(4-methoxyphenyl)-1,3,5-triazine, 2,4-bis-[{(4-(3-sulphonato)-2-hydroxy-propyloxy)-2-hydroxy}-phenyl]-6-(4-methoxyphenyl)-1,3,5-triazine sodium salt, 2,4-bis[{(3-(2-propyloxy)-2-hydroxy-propyloxy)-2-hydroxy}-phenyl]-6-(4-methoxy-phenyl)-1,3,5-triazine, 2,4-bis-[{4-(2-ethyl-hexyloxy)-2-hydroxy}-phenyl]-6-[4-(2-methoxyethyl-carbonyl)-phenylamino]-1,3,5-triazine, 2,4-bis-[{4-(3-(2-propyloxy)-2-hydroxy-propyloxy)-2-hydroxy}-phenyl]-6-[4-(2-ethylcarboxyl)-phenylamino]-1,3,5-triazine, 2,4-bis-[{4-(2-ethyl-hexyloxy)-2-hydroxy}-phenyl]-6-(1-methyl-pyrrol-2-yl-)-1,3,5-triazine, 2,4-bis-[{4-tris-(trimethylsiloxy-silylpropyloxy)-2-hydroxy}-phenyl]-6-(4-methoxyphenyl)-1,3,5-triazine, 2,4-bis-[{4-(2"-methylpropenyloxy)-2-hydroxy}-phenyl]-6-(4-methoxyphenyl)-1,3,5-triazine, 2,4-bis-[{4-(1',1',1',5',5',5'-hepta-methylsiloxy-2"-methyl-propyloxy)-2-hydroxy}-phenyl]-6-(4-methoxyphenyl)-1,3,5-triazine.

Preparations according to the invention advantageously comprise substances which absorb UV radiation, it being possible for UV-A and/or UV-B filter substances to be used. The total amount of filter substances is preferably 0.1 to 30% by weight, particularly preferably 0.2 to 10% by weight, in particular 0.5 to 5% by weight, based on the total weight of the preparation.

Moreover, it is possible to use particulate UV filters or inorganic pigments, which may be hydrophobicised, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures.

Also advantageous is the incorporation of cooling agents into the multiphase soap. Examples of cooling agents which may be mentioned are: 1-menthol, menthoneglycerol acetal, menthyl lactate, substituted menthyl-3-carboxamides (e.g. N-ethylmenthyl-3-carboxamide), 2-isopropyl-N,2,3-trimethylbutanamide, substituted cyclohexanecarboxamides, 3-menthoxypropane-1,2-diol, 2-hydroxyethyl menthylcarbonate, 2-hydroxypropyl menthylcarbonate, N-acetylglycine menthyl ester, menthyl hydroxycarboxylates (e.g. menthyl-3-hydroxybutyrate), monomenthyl succinate, 2-mercaptocyclodecanone, menthyl-2-pyrrolidin-5-onecarboxylate.

The multiphase soaps according to the invention can comprise antimicrobial active ingredients and biocides. The biocides may be hydrophilic, amphoteric or hydrophobic in nature. Examples which may be mentioned are:

lactam active ingredients and salts thereof, lactones, 2-pyridones and 2-pyrithones, α- and β-cyclodextrins, ciprofloxacin, norfloxacin, tetracyclins, erythromycin, amikacin, triclosan, deoxycycline, capreomycin, chlorhexidine, chlortetracycline, oxytetracycline, clindamycine, ethambutol, metronidazole, pentamidine, gentamicin, kanamycin, lineomycin, methacycline, minocycline, neomycin, netilmicin, paromomycin, streptomycin, tobramycin, miconazole, amantadine, quaternary monoammonium salts, such as cocoalkylbenzyldimethylammonium chloride, ($C_{12}$–$C_{14}$) alkylbenzyldimethylammonium chloride, 1-(3-chloroallyl)-3,5,7-triaza-1-azoniaadamantane chloride (Dowicil®), cocoalkyldichloro-benzyldimethylammonium chloride, tetradecylbenzyldimethylammonium chloride, didecyldimethylammonium chloride, dioctyidimethylammonium chloride, myristyltrimethylammonium bromide, cetyltrimethylammonium bromide, monoquaternary heterocyclic amine salts, such as, for example, laurylpyridinium chloride cetylpyridinium chloride, ($C_{12}$–$C_{14}$) alkylbenzylimidazolium chloride, triphenylphosphonium salts, such as, for example, myristyltriphenylphosphonium bromide, polymeric biocides, as obtainable, for example, from the reaction of epichlorohydrin and dimethylamine, diethylamine or imidazole, 1,3-dichloro-2-propanol and dimethylamine or 1,3-bis(dimethylamino)-2-propanol, ethylene dichloride and 1,3-bis(dimethylamino)-2-propanol, bis(2-chloroethyl) ether and N,N'-bis (dimethylaminopropyl)-urea or -thiourea, polymeric biguanidine hydrochlorides (e.g. Vantocil IB), derivatives of N-(N'-$C_8$–$C_{18}$-alkyl-3-aminopropyl)glycine, of N-(N'-(N"-$C_8$–$C_{18}$-alkyl-2-aminoethyl)-2-aminoethyl)glycine, of N-(N'-bis(N'-$C_8$–$C_{18}$-alkyl-2-aminoethyl)glycine, such as, for example, (dodecyl)(aminopropyl)glycine or (dodecyl) (diethylenediamine)glycine, amines, such as N-(3-aminopropyl)-N-dodecyl-1,3-propanediamine, halogenated biocides, for example hypochlorites or sodium dichloroisocyanurates, phenolic biocides, such as, for example, phenol and its derivatives, phenol ethers, monoalkyl phenols, polyalkyl phenols, arylphenols, o-phenylphenol, p-tert-butylphenol, 6-n-amyl-m-kresol, 4,4'-diamidino-, -diphenoxypropane diisethionate (propamidine isethionate), 4,4'-diamidino-, -diphenoxyhexane diisethionate (hexamidine isethionate), alkyl- and/or aryl-chloro- or -bromophenols, such as, for example, o-benzyl-p-chlorophenol, resorcinol and its derivatives, such as, for example, resorcinol monoacetate, cresoles, p-chloro-m-xylene, dichloro-m-xylene, 4-chloro-m-cresol, halogenated diphenyl ethers, such as, for example, 2',4,4'-trichloro-2-hydroxydiphenyl ether (Triclosan) or 2,2'-dihydroxy-5,5'-dibromodiphenyl ether, chlorophenesin (p-chlorophenyl glycerol ether), bisphenol compounds, bis (2-hydroxy-3,5-dichlorophenyl) sulphide, bis(2-hydroxy-5-chlorobenzyl) sulphide, halogenated carbanilides, such as, for example, 3,4,4'-trichlorocarbanilide.

Also suitable are pyrithiones, in particular the sodium and zinc compounds, Octopirox®, Nuosept®, Nuosept C®, dimethyldimethylolhydantoin (DMDM, Glydant®), 3-butyl-2-iodopropinylcarbamate, Glydant Plus®, 3-isothiazolone compounds, methylchloroisothiazolinone, diazolidinyl urea (Germall II®), imidazolidinyl urea (Abiol®, Unicide U-13®, Germall 115®), benzyl alcohol, bicyclic polymethoxyoxazolidinones (e.g. Nuosept®C), 2-bromo-2-nitropropane-1,3-diol (Bronopol®), iodopropynyl butyl carbamate (Polyphase P100®), chloroacetamide, methanamine, 1,2-dibromo-2,4-dicyanobutane (Tektamer®), 5-bromo-5-nitro-1,3-dioxane (Bronidox®), phenethyl alcohol, o-phenylphenol, sodium o-phenylphenol, sodium hydroxymethylglycinate (Suttocide A®), dimethoxane, Kathon CG®, thimerosal, dichlorobenzyl alcohol, captan, chlorophenesin, dichlorophene, chlorobutanol, glyceryl laurate.

Aryl- or aryloxy-substituted, unbranched or mono- and poly-alkyl-branched saturated or mono- to penta-unsaturated (up to five double or triple bonds, also mixed ene-yne compounds), fatty alcohols, fatty aldehydes and fatty acids of chain lengths $C_2$ to $C_{40}$.

Aryl- or aryloxy-substituted unbranched or mono- and poly-alkyl-branched saturated or mono- to penta-unsaturated (up to five double or triple bonds, also mixed ene-yne compounds), alkanediols, dialdehydes and dicarboxylic acids of chain length $C_2$ to $C_{40}$.

Mono- and oligoglycerides (up to 4 glycerol units), aryl- or aryloxy-substituted unbranched or mono- and poly-alkyl-branched saturated or mono- to penta-unsaturated (up to five double or triple bonds, also mixed ene-yne compounds), fatty alcohols (mono- and oligoglycerol monoalkyl ethers), fatty acids (mono- and oligoglycerol monoalkyl esters), alkanediols (mono- and oligoglycerol monoalkyl ethers; bis(mono/oligoglyceryl) alkyl diethers) and dicarboxylic acids (mono- and oligoglycerol monoalkyl esters; bis (mono-/oligoglyceryl) alkyl diesters) of chain lengths $C_2$ to $C_{40}$.

Fatty acid esters of unbranched or mono- and poly-alkyl-branched saturated or mono- to penta-unsaturated (up to five double or triple bonds, also mixed ene-yne compounds), optionally also aryl- or aryloxy-substituted carboxylic acids of chain lengths $C_2$ to $C_{40}$ with unbranched or mono- and poly-alkyl-branched saturated or mono- to penta-unsaturated (up to five double or triple bonds, also mixed ene-yne compounds), optionally also aryl- or aryloxy-substituted mono- to hexahydric fatty alcohols of chain lengths $C_2$ to $C_{40}$.

Vegetable and animal fatty acid cuts, comprising unbranched or mono- and poly-alkyl-branched saturated or mono- to penta-unsaturated (up to five double or triple bonds, also mixed ene-yne compounds), fatty alcohols, fatty aldehydes and fatty acids of chain lengths $C_2$ to $C_{40}$ (e.g. coconut fatty acids, palm kernel fatty acids, wool wax acids).

Mono- and oligoglycerides of lanolin, of lanolin alcohols and lanolin acids (e.g. glyceryl lanolate, neocerite), glycyrrhetic acid and derivatives (e.g. glycyrrhetinyl stearate), natural and synthetic cardenolides (e.g. digitoxin, dogoxin, digoxygenin, gitoxygenin, strophanthin and strophanthidin), natural and synthetic bufadienolides (e.g. scillaren A, scillarenin and bufotalin), sapogenins and steroid sapogenins (e.g. amyrines, oleanoic acid, digitonin, gitogenin, tigogenin and diosgenin), steroid alkaloids of vegetable and animal origin (e.g. tomatidine, solanine, solanidine, conessine, batrachotoxin and homobatrachotoxin).

Mono- and polyhalogenated nitriles, dinitriles, trinitriles or tetranitriles.

Mono- and oligohydroxy fatty acids of chain lengths $C_2$ to $C_{24}$ (e.g. lactic acid, 2-hydroxypalmitic acid), oligomers and/or polymers thereof, and vegetable and animal raw materials, comprising these.

Unsubstituted and alkyl-substituted hydroquinones, and plant extracts comprising these (e.g. sage extract, rosemary extract).

Acyclic terpenes: terpene hydrocarbons (e.g. ocimene, myrcene), terpene alcohols (e.g. geraniol, linalool, citronellol), terpene aldehydes and ketones (e.g. citral, pseudoionone, β-ionone); monocyclic terpenes: terpene hydrocarbons (e.g. terpinene, terpinolene, limonene), terpene alcohols (e.g. terpineol, thymol, menthol), terpene ketones (e.g. pulegone, carvone). Bicyclic terpenes: terpene hydrocarbons (e.g. carane, pinane, bornane), terpene alcohols (e.g. borneol, isoborneol), terpene ketones (e.g. camphor), sesquiterpenes: acyclic sesquiterpenes (e.g. farnesole, nerolidol), monocyclic sesquiterpenes (e.g. bisabolol), bicyclic sesquiterpenes (e.g. cadinene, selinene, vetivazulene, guaiazulene), tricyclic sesquiterpenes (e.g. santalene), diterpenes (e.g. phytol), tricyclic diterpenes (e.g. abietic acid), triterpenes (squalenoids; e.g. squalene), tetraterpenes.

Classic preservatives (e.g. formaldehyde, glutaraldehyde, parabens (e.g. methylparaben, ethylparaben, propylparaben and butylparaben), sorbitol, dibromodicyanobutane, imidazolidinyl ureas ("Germall"), isothiazolinones ("Kathon"), methylchlorothiazolidine, methylthiazolidine, organic acids (e.g. benzoic acid, sorbic acid, salicylic acid), and esters thereof, glycols, e.g. propylene glycol, 1,2-dihydroxyalkanes), vegetable preservative aids and flavonoids (e.g. lantadin A, caryophyllene, hesperidin, diosmin, phellandrene, pigenine, quercetin, hypericin, aucubin, diosgenin, plumbagin, corlilagin etc) and glycosylated derivatives thereof (e.g. glycosylrutin).

Ethoxylated, propoxylated or mixed ethoxylated/propoxylated cosmetic fatty alcohols, fatty acids and fatty acid esters of chain lengths $C_2$ to $C_{40}$ with 1 to 150 E/O and/or P/O units.

Antimicrobial peptides and proteins having an amino acid number of 4 to 200, e.g. magainins, magainin amides, PGLa, PYLa, PGSa, xenopsin, xenopsin precursor fragments [XPFs], caerulein, caerulein precursor fragments [CPFs], caeridins, brevinins, esculentins, bombinins, derma-septins, tachyplesins, polyphemusins, lantibiotics [e.g. epidermin, gallidermin, nisin, subtilin, Pep5, pediocins, plantaricins, leucocins, cinnamycin, duramycin, ancovenin, colicins, pyocins, bacteriocins, microcins, lactococcins, lactacins, mersacidins, actagardins, lacticins, streptococcins, salivarins, carnocins, lactocins, lanthiopeptins etc.], skin antimicrobial peptides (SAPs), lingual antimicrobial peptides (LAPs), human β-defensins (in particular h-BD1 and h-BD2), tracheal antimicrobial peptides (TAPs), defensins, neutrophil peptides [e.g. NP-1 to NP-5; HNP-1 to HNP-4; GPNP; cryptidins; RatNP-1 to RatNP-4, sapecins, drosocins, cecropins, andropins, attacins, sarcotoxins, diptericins, coelopterins, apidecins, abecins, hymenoptecins, melittins, *Aedes aegyptii* defensins, cathepsin D, azurocidins, lactoferrins and their hyrolysates and peptides obtained therefrom, bactericidal/permeability increasing proteins [BPIs], elastases, cationic microbial proteins [CAPs], lysozyme, serprocidins, myeloperoxidase, indolicidins; major basic proteins [MBPs], eosinophil cationic proteins [ECPs]; bactenecins; macrophage cationic peptides [MCPs], histatins, amebapores, thionines, cysteine-rich antimicrobial peptides from plants (e.g. Mj-AMPs, Ac-AMPs, Rs-AFPs, Rs-nsLTPs, Rs-2S) and their synthetic analogues comprising L- and/or D-amino acids (e.g. MSI-78).

Highly suitable carbohydrates or "carbohydrate derivatives" which, abbreviated, should also come under the name "carbohydrates", are sugars and substituted sugars or compounds containing sugar radicals. The sugars in particular also in each case include the deoxy and dideoxy forms. Highly suitable monosaccharides are, for example, tetroses, pentoses, hexoses and heptoses. Pentoses and hexoses are preferred. The ring structures include furanoses and pyranoses, and both D- and L-isomers, as well as α- and β-anomers, are included. The deoxy and dideoxy forms are also suitable.

Highly suitable disaccharides are, for example, the disaccharides formed by binary linkages of the above monosaccharides. Linkage can take place as an α- or β-glycosidic bond between the two subunits. Sucrose, maltose and lactobiose are preferred. N-acetylgalactosamine and N-acetylglucosamine derivatives and also sialic acid-substituted derivatives are likewise suitable.

Highly suitable oligosaccharides consist of a number, e.g. 2–7, sugar units, preferably of the sugars described under mono- and disaccharides, in particular consisting of 2 to 5 units in the known bonding forms resulting by condensation and as mentioned above. In addition to the disaccharides, particularly preferred oligosaccharides are the tri- and tetrasaccharides. Likewise suitable are N-acetylgalactosamine and N-acetylglucosamine derivatives and also sialic acid-substituted derivatives.

Mono-, di- and oligosaccharides, in particular as described above, having one or more amino groups which can be acylated, in particular acetylated, are suitable. Ribosylamine; N-acetylglucosamine and N-galactosylamine and sialic acid-substituted derivatives are preferred.

Furthermore, sugar esters of organic or inorganic acids are advantageously used, for example sugar phosphates, sugar esters with carboxylic acids or sulphated sugars, in particular esters of the sugars described above.

Preferred sugar esters of phosphoric acid are glucose 1-phosphate; fructose 1-phosphate, glucose 6-phosphate or mannose 6-phosphate.

Preferred esters of sugars and carboxylic acids are obtained with carboxylic acids of chain length $C_1$ to $C_{24}$, for example cetearyl glucoside, caprylyl/capryl glucoside, decyl glucoside, sucrose laurate and myristate, sucrose cocoate but in particular also the sugar acetates, preferably of the above sugars.

Also preferred are the sugar ethers of sugars, in particular of the above sugars, with mono- and polyhydric alcohols of chain length $C_1$ to $C_{24}$, e.g. Plantaren® 1200 (from Henkel) or Plantaren® 2000 (from Henkel).

Also suitable are the reaction products of sugars with ethylene oxide and/or propylene oxide, for example, preferably with the above sugars. E/O or P/O grades of one to 40 ether units are suitable.

The polysaccharides can be unbranched or branched and both the homopolysaccharides and the heteropolysaccharides, in each case in particular with such sugars as described above, are suitable. Preferred polysaccharides are starch, glycogen, cellulose, dextran, tunicin, inulin, chitin, in particular chitosans, chitin hydrolysates, alginic acid and alginates, plant gums, body mucins, pectins, mannans, galactans, xylans, araban, polyoses, chondroitin sulphates, heparin, hyaluronic acid and glycosaminoglycans, hemicelluloses, substituted cellulose and substituted starch, in particular in each case the hydroxyalkyl-substituted polysaccharides.

Amylose, amylopectin, xanthan, α-, β- and γ-dextrin are particularly suitable. The polysaccharides can consist, for example, of 4 to 1 000 000, in particular 10 to 100 000, monosaccharides. Preferably, in each case those chain lengths are selected which guarantee that the active compound is soluble in the respective preparation or can be incorporated in it.

Spingolipids such as sphingosine; N-monoalkylated sphingosines; N,N-dialkylated sphingosines; sphingosine-1-phosphate; sphingosine-1-sulphate; psychosine (sphingosine-β-D-galactopyranoside); sphingosylphosphorylcholine; lysosulphatide (sphingosyl-galactosyl sulphate; lysocerebroside sulphate); lecithin; sphingomyelin; sphinganine.

It is also possible to use "natural" antibacterial active ingredients; these are mostly essential oils. Typical antibacterially active oils are, for example, oils of anise, lemon, orange, rosemary, wintergreen, thyme, lavender, hops, citronella, wheat, lemongrass, cedarwood, cinnamon, geranium, sandalwood, violet, eucalyptus, peppermint, gum benzoin, basil, fennel, menthol and *Ocmea origanum, Hydastis carradensis, Berberidaceae daceae,* Ratanhiae or *Curcuma longa.*

Important antimicrobially active substances which can be found in essential oils are, for example, anethole, catechole, camphene, carvacrol, eugenol, eucalyptol, ferulic acid, famesol, hinokitiol, tropolone, limonene, menthol, methyl salicylate, thymol, terpineol, verbenone, berberine, curcumin, caryophyllene oxide, nerolidol, geraniol.

It is also possible to use mixtures of said active systems or active ingredients and also active ingredient combinations comprising these active ingredients.

The amount of active ingredients in the preparations is preferably 0.01 to 20% by weight, based on the total weight of the preparations, particularly preferably 0.05–10% by weight.

The multiphase soaps according to the invention can comprise insect repellents, i.e. active ingredients against insects ("repellents"): repellents are agents which are intended to prevent insects contacting with the skin and becoming active thereon. They drive away the animals and evaporate slowly. The most frequently used repellent is diethyl toluamide (DEET). Further customary repellents are given in "Pflegekosmetik" [care cosmetics], W. Raab, U. Kindl, Gustav-Fischer-Verlag Stuttgart/New York, 1991, p. 161, and Ullmann's Encyclopedia of Industrial Chemistry, VCH Weinheim 1989, Vol. A14, pp. 305–308.

It is also possible to use natural repellents, such as anise oil, bergamot oil, cedarwood oil, citronella oil, citrus peel oils, eucalyptus oil, spruce needle oil, lavandin oil, lavender oil, Leptospermum petersonii oil, bay leaf oil, massoi oil, Mentha arvensis oil, nutmeg oil, clove leaf oil, clove flower oil, neroli oil, origanum oil, peppermint oil, pennyroyal oil, spike lavender oil, tagetes oil, tea tree oil, thyme oil, vetiver oil, cinnamon leaf oil and cinnamon bark oil or mixtures-thereof; fragrances such as δ-decalactone, γ-decalactone, δ-dodecalactone, γ-dodecalactone, (E,Z)-2,6-nonadienal, δ-nonalactone, γ-nonalactone, δ-octalactone, γ-octalactone, α-phellandrene, δ-undecalactone, γ-undecalactone, 1,8-cineol, 1-phenyl-1,3-propanediol, 2-nonenal, 3,4-dihydrocoumarin, 3,8-p-menthanediol, 4a,5,6,7,8,8a-hexahydrocoumarin, 8-acetoxy-2-menthanone, benzyl benzoate, camphor, citronellol, coumarin, geraniol, linalool, octahydrocoumarin, piperitone, pulegone, hexylcinnamaldehyde (3-hexyl-3-phenyl-2-propenal), cinnamaldehyde, coniferyl aldehyde or mixtures thereof; synthetic repellents, such as N,N-diethyltoluamide(N,N-diethy-3-1-methylbenzamide, DEET), bis-(dimethylthiocarbamoyl) disulphide (thiram), ethylenebis(dithiocarbamic acid) disodium salt (nabam), butoxypoly(propylene glycol), N-butylacetanilide, 2,3,4,5-bis(butyl-2-ene) tetrahydrofurfural, butyl 3,4-dihydro-2,2-dimethyl-4-oxo-2H-pyran-6-carboxylate, dibutyl adiptate, di-n-butylsuccinate, 2-butyl-2-ethyl-1,3-propanediol, di-n-propylpyridine 2,5-dicarboxylate, isobutyl 2-(2-hydroxyethyl)piperidine-1-carboxylate, dibutyl phthalate, dimethyl phthalate, indalone and 2-ethyl-1,3-hexanediol or mixtures thereof.

Particular preference is given to isobutyl 2-(2-hydroxyethyl)piperidine-1-carboxylate and N,N-diethyltoluamide or repellent mixtures comprising these compounds.

Further suitable insecticide classes which may be mentioned are: synthetic pyrethroids (e.g. chrysanthemates and analogues thereof) or natural pyrethroids (e.g. pyrethrins, cinerins, jasmolins), phenyl acetate esters, dinitrophenols and derivatives thereof, juvenoids (such as, for example, substituted 2,6-nonadienoates or 2,4-dodecadienoates), ethyl [2-(4-phenoxyphenoxy)-ethyl]carbamate, 2-ethyl-3-[3-ethyl-5-(4-ethylphenoxy)-pentyl]-2-methyloxirane, rotenones (e.g. elliptone, sumatrol, 15-hydroxyrotenone, malaccol, L-a-toxicarol, 15-hydroxyelliptone, deguelin), sabadilla preparations obtainable from ground seeds of Schoenocaulon officinale (Liliaceae), preparations obtainable from Ryania speciosa (Flacourtiaceae), ryanodin, azadirachtin, extracts of the neem tree (Azadirachta indica), organophosphorous insecticides, such as, for example, phosphorous anhydrides, vinyl phosphates, aliphatic phosphorothioates, phosphorothioates of phenols, phosphonothioates of phenols, organophosphoric esters, dimethyl carbamates of heterocyclic enols. It is possible to use mixtures or combinations of said repellents.

The multiphase soaps according to the invention can comprise deodorants, i.e. active ingredients with a deodorizing and antiperspirant action. These include antiperspirants based on aluminium, zirconium or zinc salts, deodorants, bactericides or bacteriostatic deodorizing substances, such as, for example, triclosan, hexachlorophene, triclocarban, alcohols and cation-active substances, such as, for example, quaternary ammonium salts and odour absorbers, such as, for example, ®Grillocin (combination of zinc ricinoleate and various additives) or triethyl citrate, optionally in combination with an antioxidant, such as, for example, butylhydroxytoluene or ion exchange resins. In antiperspirants, astringents—predominantly aluminium salts, such as aluminium hydroxychloride (aluminium chlorohydrate)—can suppress the formation of perspiration.

According to the invention, the multiphase soaps can comprise antioxidants or preservatives. Antioxidants or preservatives which can be used are all antioxidants customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, λ-linoleyl, cholesteryl, glyceryl and oligoglyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulphoximine compounds (e.g. buthionine sulphoximines, homocysteine sulphoximine, buthionine sulphones, penta-, hexa-, heptathionine sulphoximine) in very low tolerated doses (e.g. pmol to μmol/kg), also (metal) chelating agents (e.g. α-hydroxy fatty acids, palmitic acid, phytic acid, lactoferrine, α-hydroxy acids (e.g. citric acid, lactic acid, malic acid), humic acid, bile acid, bile extracts, tannins, bilirubin, biliverdin, EDTA, EGTA and derivatives thereof, unsaturated fatty acids and derivatives thereof (e.g. γ-linolenic acid, linoleic acid, oleic acid) folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, ferulic acid and derivatives thereof, caffeic acid and derivatives thereof, sinapic acid and derivatives thereof, curcuminoids and derivatives thereof, retinoids, ursolic acid, levulic acid, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof, (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention. Natural extracts, e.g. from green tea, algae, grape seeds, wheatgerms, rosemary, flavonoids, quercetin, phenolic benzylamines.

Also suitable are coenzymes, such as, for example, coenzyme Q10, plastoquinone, menaquinone, ubiquinols 1–10, ubiquinones 1–10 or derivatives of these substances.

The amount of antioxidants (one or more compounds) in the preparations is preferably 0.01 to 20% by weight, particularly preferably 0.05–10% by weight, in particular 0.2–5% by weight, based on the total weight of the preparation.

If vitamin E and/or derivatives thereof represent the antioxidant(s), it is advantageous to choose their respective concentrations from the range from 0.001 to 10% by weight, based on the total weight of the formulation.

If vitamin A or vitamin A derivatives, or carotenes or derivatives thereof represent the antioxidant(s), it is advantageous to choose their respective concentrations from the range from 0.001 to 10% by weight, based on the total weight of the formulation.

The multiphase soaps according to the invention can comprise moisture regulators. The moisture regulators ("moisturizers") used are, for example, the following substances: sodium lactate, urea, alcohols, sorbitol, glycerol, propylene glycol, collagen, elastin or hyaluronic acid, diacyl adipates, petroleum, ectoin, urocanic acid, lecithin, pantheol, phytantriol, lycopene, algae extract, ceramides, cholesterol, glycolipids, chitosan, chondroitin sulphate, polyamino acids and sugars, lanolin, lanolin esters, amino acids, alpha-hydroxy acids (e.g. citric acid, lactic acid, malic acid) and derivatives thereof, sugars (e.g. inositol), alpha-hydroxy fatty acids, phytosteroles, triterpene acids, such as betulinic acid or ursolic acid, algae extracts.

The multiphase soaps according to the invention can comprise skin-lightening substances, such as, for example, ascorbyl phosphate, alpha-hydroxy acids (e.g. citric acid, lactic acid, malic acid) and derivatives thereof, inhibitors of the nitrogen oxide synthesis, such as, for example, L-nitroarginine and derivatives thereof, 2,7-dinitroindazole or thiocitrulline, metal chelating agents (e.g. $\alpha$-hydroxy fatty acids, palmitic acid, phytic acid, lactoferrin, $\alpha$-hydroxy acids (e.g. citric acid, lactic acid, malic acid), humic acid, bile acid, bile extracts, bilirubin, biliverdin, EDTA, EGTA and derivatives thereof, arbutin, kojic acid, hydroquinone, resorcinol, flavonoids, retinoids, soya milk, serine protease inhibitors or lipoic acid.

It is also advantageous to incorporate active ingredients from the group of refatting substances into the multiphase soaps, such as, for example, Purcellinol®, Eucerit® and Neocerit®.

The multiphase soaps according to the invention can also comprise skin-regenerating complexes (skin repair complex), which are obtainable, for example, from inactivated and disintegrated cultures of bacteria of the Bifidus group.

The multiphase soaps according to the invention can also comprise self-tanning agents, such as dihydroxyacetone, glyceraldehyde, indole and derivatives thereof.

The multiphase soaps according to the invention can comprise active ingredients having a keratoplastic effect, such as, for example, benzoyl peroxide, retinoic acid, colloidal sulphur or resorcinol.

The multiphase soaps according to the invention can comprise hair-smoothing agents. For the purposes of the invention, hair-smoothing agents are substances which lead to the human or animal hair being smoothed. Suitable hair-smoothing agents are, for example, ammonium hydroxide, ammonium thioglycolate, calcium hydroxide and sodium hydroxide.

The multiphase soaps according to the invention can comprise hair-removal agents. For purposes of the invention, hair-removal agents are substances which lead to human or animal hair being removed from the skin.

Suitable hair-removal agents are, for example, barium sulphide, magnesium thioglycolate, strontium sulphide, calcium sulphide, thiopropionic acid, strontium thioglycolate, calcium thioglycolate, potassium sulphide, thioglycerol, ethanolamine thioglycolate, potassium thioglycolate, thioglycolic acid, lithium sulphide, sodium sulphide, thiolactic acid, magnesium sulphide, ammonium thioglycolate and sodium thio-glycolate.

The multiphase soaps according to the invention can also comprise antidandruff active ingredients, such as, for example, climbazole, ketoconazole or zinc pyrithione.

According to the invention, the active ingredients present in the multiphase soaps can likewise be chosen advantageously from the following group, preference being given to oily or oil-soluble active ingredients: acetylsalicylic acid, atropine, azulene, hydrocortisone and derivatives thereof, e.g. hydrocortison-17 valerate, vitamins, e.g. vitamin A and derivatives, ascorbic acid and derivatives thereof, vitamins of the B and D series, very favourably vitamin $B_1$, vitamin $B_{12}$, niacinamide (nicotinamide), vitamin $D_1$, vitamin E (tocopherol) and derivatives thereof, vitamin F, panthenol, pantothenic acid, folic acid, and combinations thereof, but also bisabolol, unsaturated fatty acids, namely the essential fatty acides (often also called vitamin F), in particular $\gamma$-linolenic acid, oleic acid, eicosapentaenoic acid, docosahexanoic acid and derivatives thereof, chloramphenicol, caffeine, prostaglandines, thymol, camphor, extracts or other products of a vegetable and animal origin, e.g. evening primrose oil, borage oil or currant seed oil, fish oils, cod-liver oil or else ceramides and ceramide-like compounds and so on, vitamin-based extracts: active ingredient compositions primarily containing vitamin A, C, E, $B_1$, $B_{12}$, folic acid and biotin, amino acids and ferments, and compounds of the trace elements magnesium, silicone, phosphorus, calcium, manganese, iron or copper.

Vitamins, such as, for example, vitamins A and E, can be incorporated to vitalize the skin.

Substances with a warming effect can advantageously be incorporated into the multiphase soaps according to the invention, such as, for example, capsaicin; dihydrocapsaicin; gingerol; paradol; shogaol; piperin; paprika powder, chilli pepper powder, extracts of paprika, extracts of pepper; extracts of chilli pepper; extracts of root ginger; extracts of Aframomum melgueta, extracts of spilanthesacmella; extracts from Kaempferia galanga; extracts of Alpinia galanga, N-vanillylcarboxamides, in particular N-vanillylnonanamide; 2-nonenamides, in particular N-isobutyl-2-nonenamide; N-4-hydroxy-3-methoxyphenyl-2-nonenamide; alkyl ethers of 4-hydroxy-3-methoxybenzyl alcohol, in particular 4-hydroxy-3-methoxybenzyl n-butyl ether; alkyl ethers of 3-hydroxy-4-methoxybenzyl alcohol; alkyl ethers of 3,4-dimethxoybenzyl alcohol; alkyl ethers of 3-ethoxy-4-hydroxybenzyl alcohol; alkyl ethers of 3,4-methylenedioxybenzyl alcohol; (4-hydroxy-3-methoxyphenyl)acetamides, in particular N-n-octyl-(4-hydroxy-3-methoxyphenyl) acetamide; nicotin aldehyde;

methyl nicotinate; propyl nicotinate, 2-butoxyethyl nicotinate, benzyl nicotinate and 1-acetoxychavicol.

In addition, the following ingredients and materials, for example, are possible: vegetable waxes and oils, such as, for example, cocoa bufter, almond oil, avocado oil or jojoba oil for improving the feel of the skin, vegetable extracts, minerals, stabilizers, such as, for example, DTPA and EDTA, filling materials, such as, for example, starch and cellulose, hardeners, such as, for example, sodium chloride and sodium sulphate. In some instances, it is possible and advantageous to incorporate pharmaceutical active ingredients into the preparations according to the invention. According to the invention, all classes of active ingredient in principle are suitable. Examples are: antihistamines, antiphlogistics, antibiotics, antimycotics, active ingredients which promote circulation, keratolytics, hormones or steroids.

Substances to protect against chemical and mechanical influences can advantageously be incorporated into the multiphase soaps according to the invention. These include substances which form a barrier between the skin and external noxae, such as, for example, paraffin oils, silicone oils, plant oils, PCL products and lanolin for protection against aqueous solutions, film formers, such as sodium alginate, triethanolamine alginate, polyacrylate, polyvinyl alcohol or cellulose ethers against the effect of organic solvents, or substances based on mineral oils, plant oils or silicone oils as "lubricants" against strong mechanical stresses of the skin.

Abrasives customary in cosmetic and dermatological preparations may be used in the multiphase soaps according to the invention. Natural or synthetic minerals which can have an abrading or abrasive action are, for example, dolomite, calcium carbonate, aragonite, fel spar, aluminium oxide, silicon dioxide, quartz, quarzite, gypsum, pumice, calcite, limestone, lime, imitation marble, marble, zirconium oxide, titanium dioxide, talc, sand, quartz sand, zirconium silicate, bentonites, precipitated chalk, magnesium carbonate, almond, peach and apricot kernel flour, wheatgerm flour, rice cornflour, olive kernel flour and walnut kernel flour. Pumice, calcite, limestone, lime, chalk, imitation marble or marble are particularly suitable.

The hardness of the abrasive is preferably in the range from 1 to 4 on the Mohs' scale. The particle size is advantageously in the range 1 to 70, preferably in the range 1 to 60, particularly in the range 1 to 50 micrometres. The total amount of abrasives (one or more) in the preparations is preferably 1 to 30% by weight, preferably 10–20% by weight, based on the total weight of the preparation.

It is also possible to incorporate three-dimensional objects into the multiphase soaps. For the purposes of the invention, three-dimensional objects are objects of any shape. For example, it is possible to incorporate round, oval, rectangular, quadratic, spherical, ellipsoidal, cuboid, helical or irregularly shaped objects into soaps.

In general, the three-dimensional objects can serve for advertising purposes, as toys, e.g. in the form of figures, to unambiguously identify a brand, as collectable objects or as identifying object in cases of prize competitions.

Preference is also given to the use of one or more three-dimensional objects in one, in two or more, simultaneously in two or more soap phases, or in one or more soap phases and simultaneously outside the soap, which consist of one or more different materials.

These three-dimensional objects are preferably incorporated into the transparent part in order to obtain a visual experience before the soap is used. It is also preferred to incorporate these three-dimensional objects into the opaque part in order to achieve a surprise effect as the soap is washed away.

The incorporated three-dimensional objects should have no negative interaction with the multiphase soap, but may, for example, have a positive influence on the stability.

The three-dimensional objects can be made from a very wide variety of materials. Thus, for example, the objects can be made of soap mass, plastic, metal, ceramic, wood, textiles, glass, minerals, parts of plants, leather, cardboard or paper.

Preference is given to the use of plastics such as, for example, polyurethanes, polyethylenes, polypropylenes, polystyrenes, polyacrylates and the like.

Preference is given to the use of metals, such as, for example, steel, copper, titanium, gold, silver, platinum, brass, bronze and aluminium.

Preference is given to the use of ceramics made from, for example, porcelains and clays.

Preference is given to the use of woods, such as, for example, teak, mahogany, oak, ebony, pine, spruce, beech, birch, cherry tree, walnut, meranti, yew and ash.

In the case of the use of textiles, preference is given to natural fibres, e.g. cotton, silk, shear wool or artificial fibres as textiles which are located both within and also outside of the soap bar.

Preference is given to the use of normal minerals, such as, for example, granite, sandstone, quartz, and also precious minerals, such as, for example, ruby, emerald, topaz, diamond or amethyst.

Preference is given to the use of parts of plants, such as, for example, flowers, leaves, fruits, seeds, roots, rinds and stems of a very wide variety of plants.

Preference is given to the use of naturally textured or embossed leathers from, for example, snakes, crocodiles, cattle, pigs and sheep.

The multiphase soaps according to the invention can be packaged in known packaging systems, such as, for example, winders, hard cardboard, tubes and blister packs. The type of packaging ensures here that the multiphase soap remains undamaged in shape and appearance.

The packaging systems can surround the multiphase soap either tightly or loosely. For this purpose, it is possible to use various materials, such as paper, cardboard, plastic, textiles or wood, or combinations thereof.

The packaging systems can be flexible in their design, such as, for example, films or papers, or rigid, such as, for example, hard paper or plastic cases. In addition, it is also possible to use combinations of flexible and rigid packagings.

The multiphase soaps according to the invention can either be packaged individually or else in groups of two or more. In cases of two or more soap bars in one packaging, the individual soap bars can each still be packaged separately.

The packaging materials may be transparent, such as, for example, plastic films, semi-transparent, such as, for example, plastic films or papers, non-transparent, such as, for example, papers or cardboards. In addition, combinations of transparent, semitransparent or non-transparent packagings are also suitable for multiphase soaps.

Preference is given to packaging systems for the multiphase soaps in which the multiphase nature of the soap bar can even be recognized through the transparent, partially transparent or semitransparent packaging material. In addition, preference is given to packaging systems in which the multiphase soap bar can be recognized by pressing onto the non-transparent packaging.

We have also found a process for the preparation of the multiphase soaps according to the present invention, which is characterized in that the individual phases in the form of soap strands are diagonally cut precisely at an angle of from 14° to 70°, preferably 30 to 55°, and the points of intersection are joined under pressure so that cambering arises at the points of intersection.

The phases at the points of intersection are preferably joined using a pressure of from 4 to 10 bar or with a pressing weight of 1.0 to 2.0 t. A particularly preferred cambering of the points of intersection arises under these conditions.

The soap strands are prepared in a manner known per se: after the addition of additives to the soap base, milling and extrusion are carried out. Furthermore, during industrial production, the additives may be added during extrusion (Soaps and Detergents, Luis Spitz, 0-935315-72-1 and Production of Soap, D. Osteroth, 3-921956-55-2).

Figure 3A:
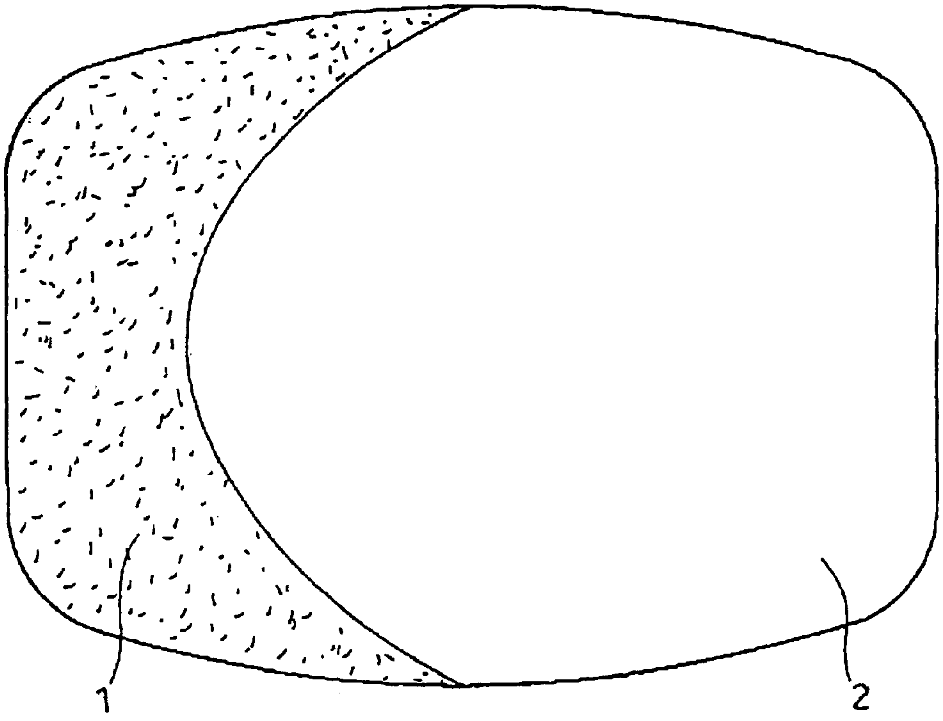
FIG. 3A shows a top cross sectional view of a two-phase soap according to the present invention.
Figure 3B:
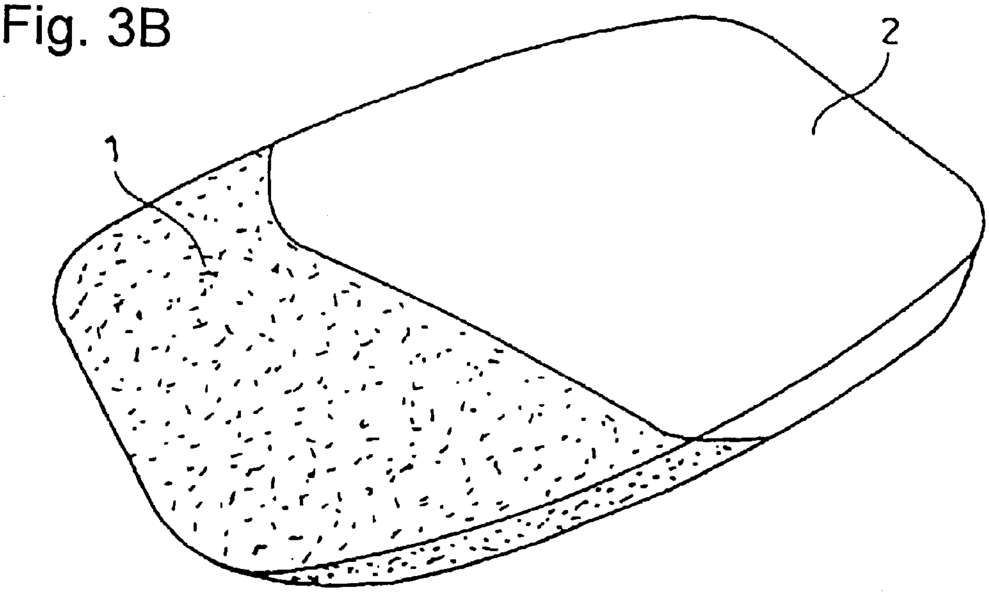
FIG. 3B shows a perspective view of the soap of FIG. 3A.

The multiphase soaps according to the present invention can be illustrated using the example of FIG. 3: FIG. 3 shows the multiphase soap according to the present invention in perspective view (FIG. 3B) and when viewed from above (FIG. 3A). The different phases are labelled 1 and 2. The diagram also depicts the cambering of the two phases.

The multiphase soaps according to the present invention surprisingly have high stability and can be prepared favorably in large bar numbers.

The invention is further illustrated but is not intended to be limited by the following examples in which all parts and percentages are by weight unless otherwise specified.

EXAMPLES

Figure 4A:
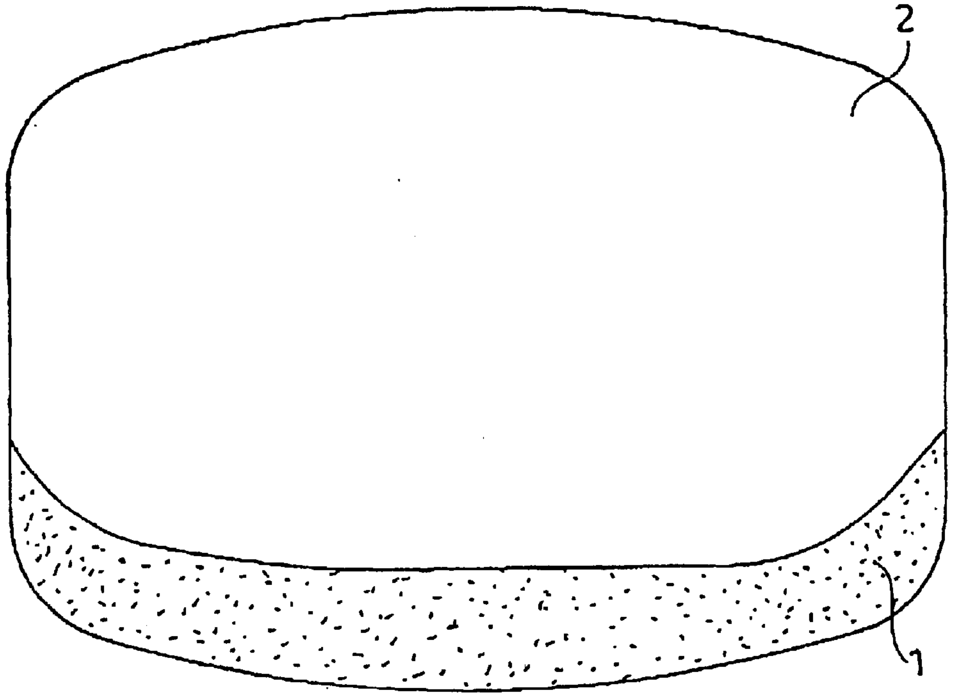
FIG. 4A shows a top view of a two-phase soap with a longitudinal section.
Figure 4B:
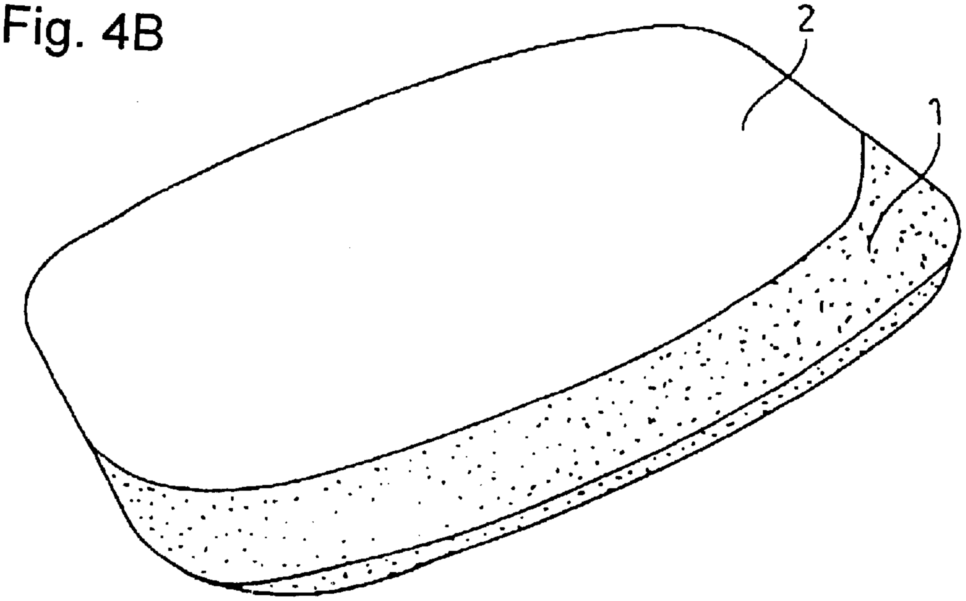
FIG. 4B shows a perspective view of the two-phase soap of FIG. 4A.

Using the example of a rounded standard soap shape (FIGS. 1A and 1B perspective view of a standard soap) with a length of 7.4 cm, a height of 1.8 cm and a width of 5.4 cm, the intersection shapes according to the present invention in the longitudinal and in the transverse direction of the multiphase soap are described below (FIGS. 3A and 3B transverse type central section, perspective view and FIGS. 4A and 4B longitudinal type central section, perspective view). This is only one application example since the different soap shapes can vary significantly in their length, height and width.

A soap bar of standard shape can be divided into two or more parts. For the purposes of the present invention, this division is in the direction of the longitudinal or transverse axis of the bar of soap at an angle between 0 and 90°. From this arise bars of soap with different types of intersection (FIGS. 5A and 5B, transverse type central section and FIGS. 6A and 6B, longitudinal type central section) and varying ratios of the viewing areas of the individual soap phases. The actual cutting angle arises as a result of the area ratios to be achieved which are necessary for distinguishing the individual soap phases. Depending on the ratio of the height to the length of the standard soap described of about 3.44, an angle of the cutting surface between the soap phases of about 14° to 60° then arises for the transverse type and an angle of about 20° to 70° for the longitudinal type. This new cutting angle varies depending on the shape of the soap and is industrially a new type of requirement during the preparation of the soap and differs significantly from the customary cutting angles of 0° (horizontal section, FIGS. 2A and 2B) or 90° (vertical section, FIGS. 7A–7B, 8A–8B and 9A–9B).

Figure 5A:
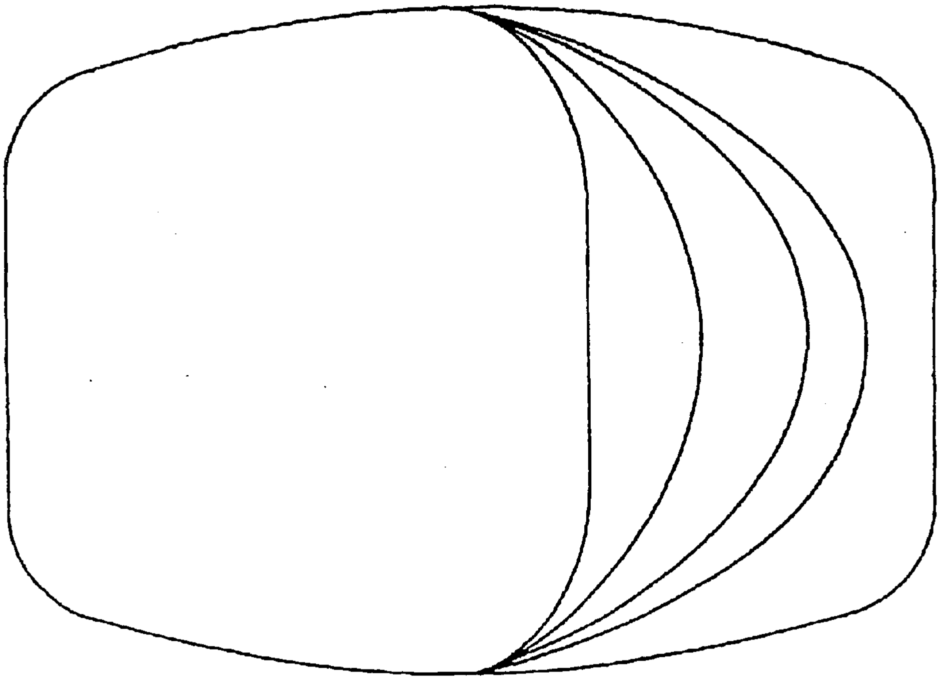
FIG. 5A shows a top view of a multiphase soap with different cutting angles.
Figure 5B:
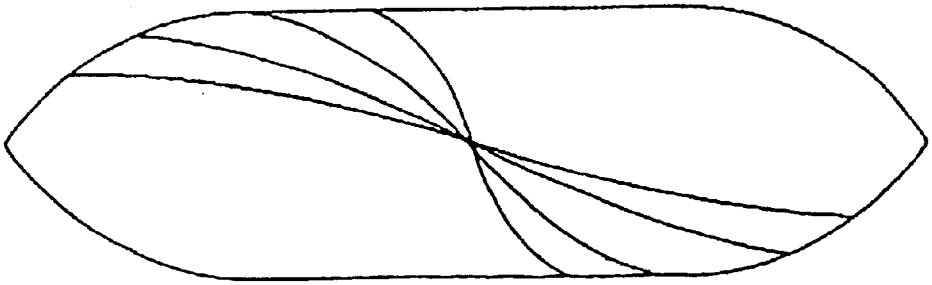
FIG. 5B shows a side view of the multiphase soap of FIG. 5A.
Figure 6A:
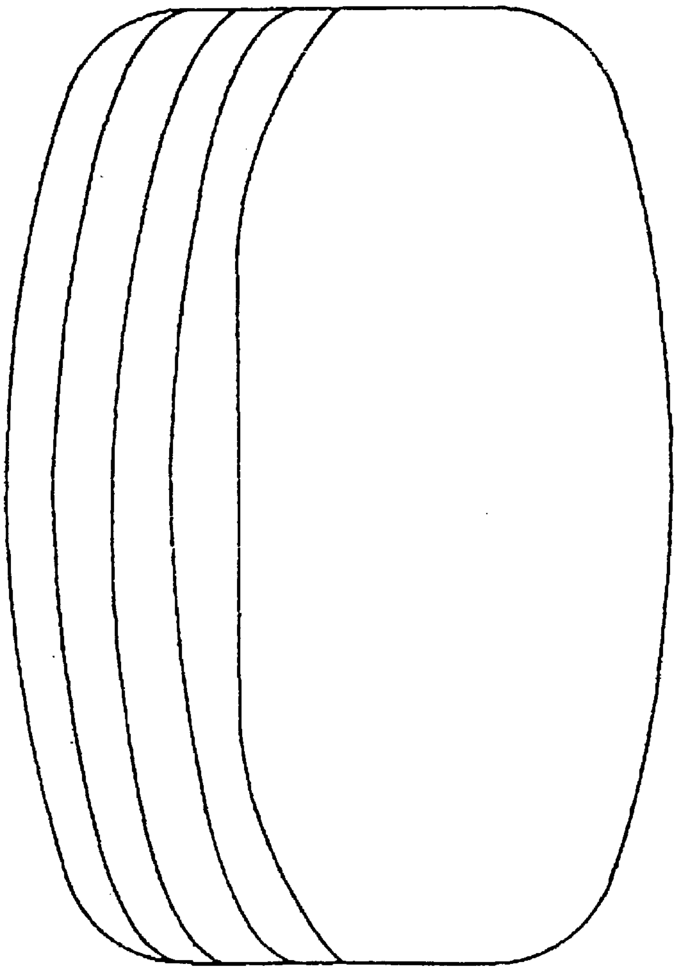
FIG. 6A shows a top view of a multiphase soap with different cutting angles of the longitudinal type.
Figure 6B:
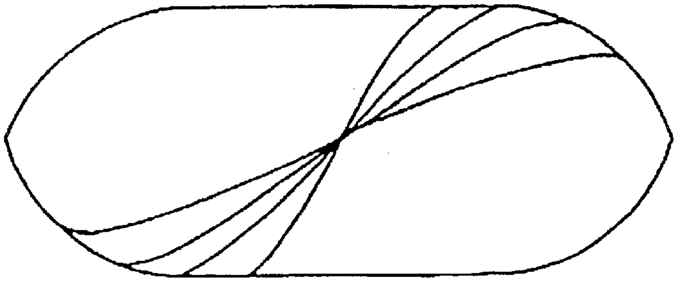
FIG. 6B shows a side view of the multiphase soap of FIG. 6A.
Figure 10A:
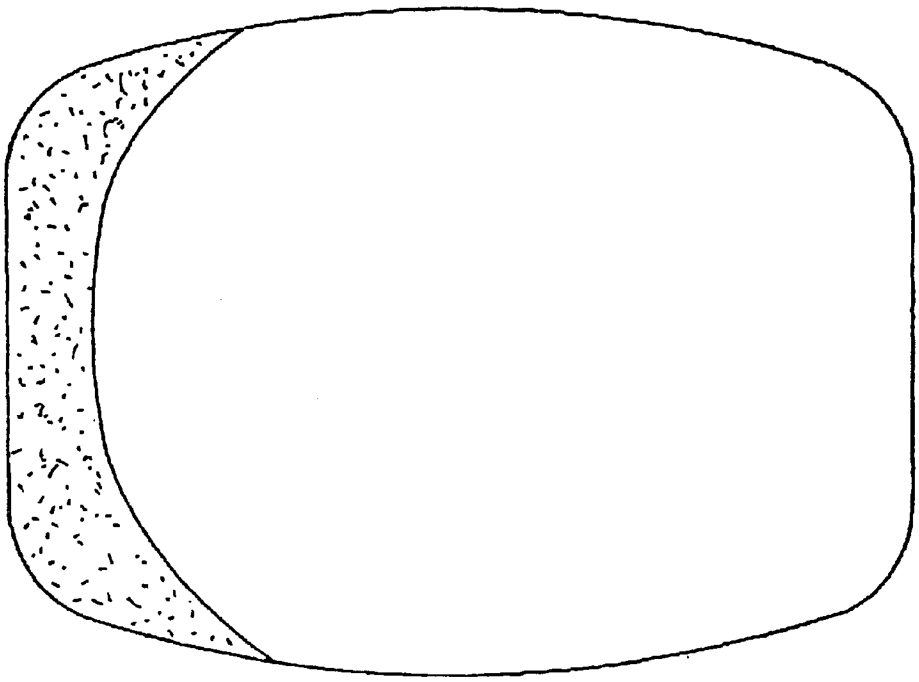
FIG. 10A shows a top view of a transverse type, displaced section through a two-phase soap.
Figure 10B:
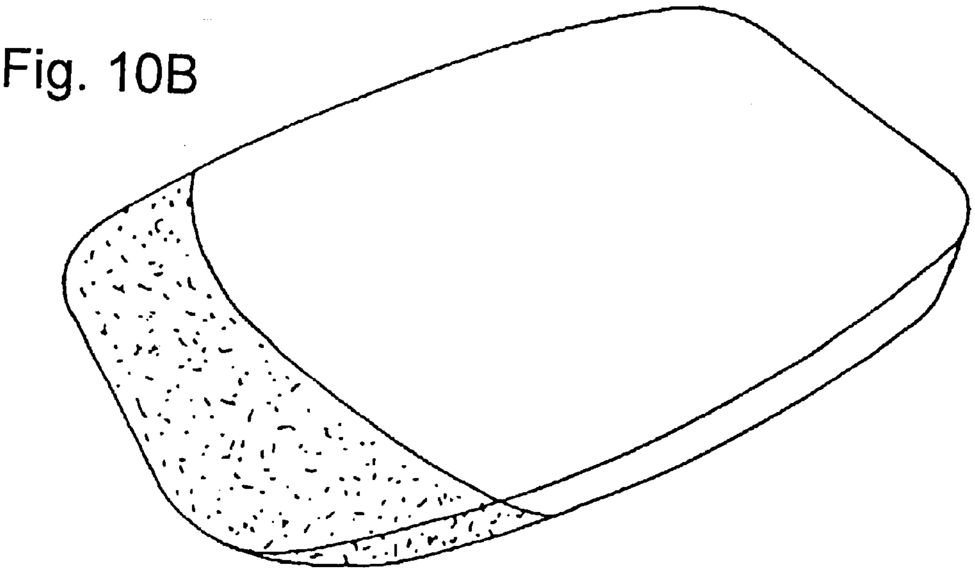
FIG. 10B shows a perspective view of the soap of FIG. 10A.

In a two-phase soap of the new diagonal type, the quantitative ratio of the two phases is identical (irrespective of the cutting direction and the cutting angle) provided the cutting point goes through the middle point of the soap (FIGS. 5A and 5B transverse type central section and FIGS. 6A and 6B). If the cutting point in the case of a two-phase soap of the novel diagonal type lies outside the middle point, for example as a result of horizontal or vertical shifting of the sectional area, a bar of soap with differently sized phases results (FIGS. 10A and 10B, transverse type of displaced section).

Application Test:

1. Durability Test of Different Multiphase Soaps

Figure 11:
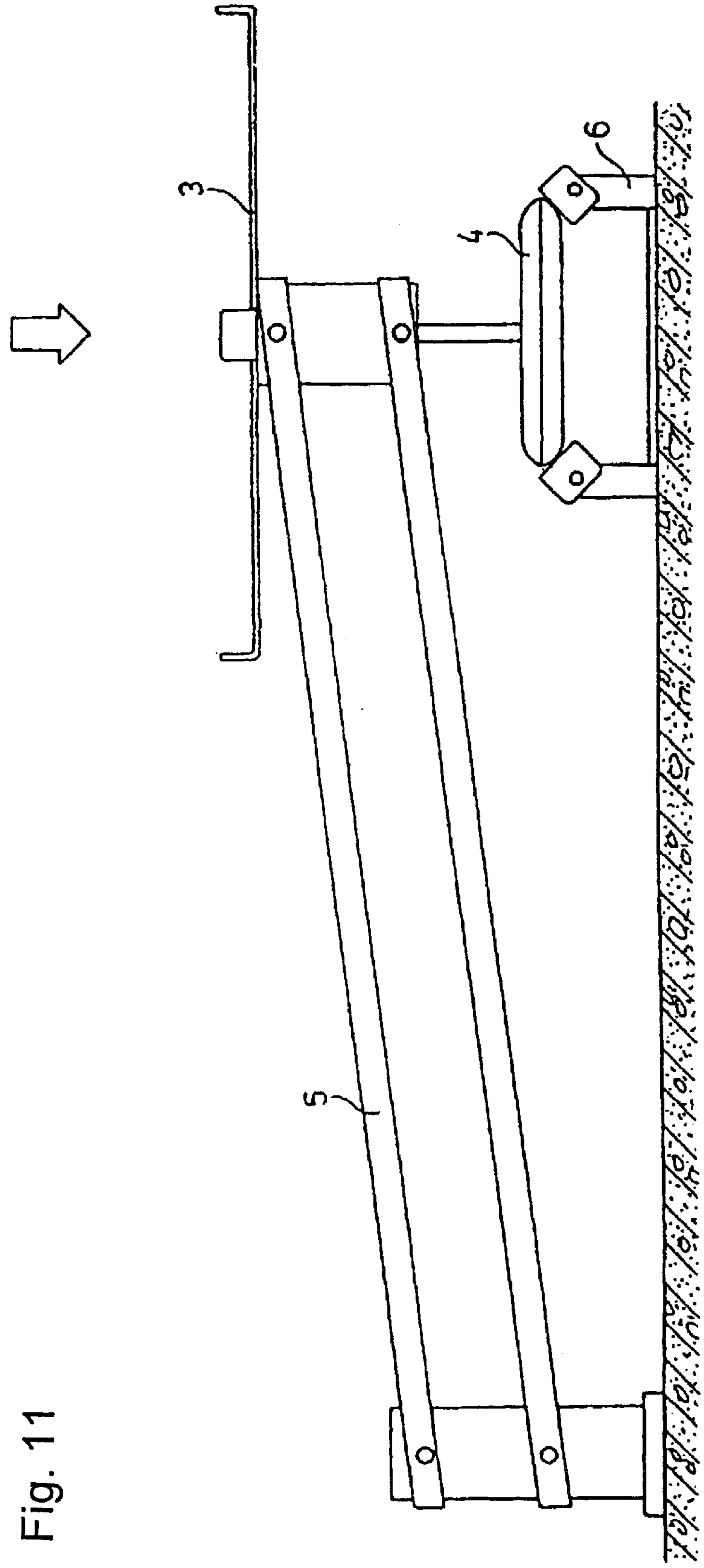
FIG. 11 shows a measuring device for fracture tests.
Figure 12A:
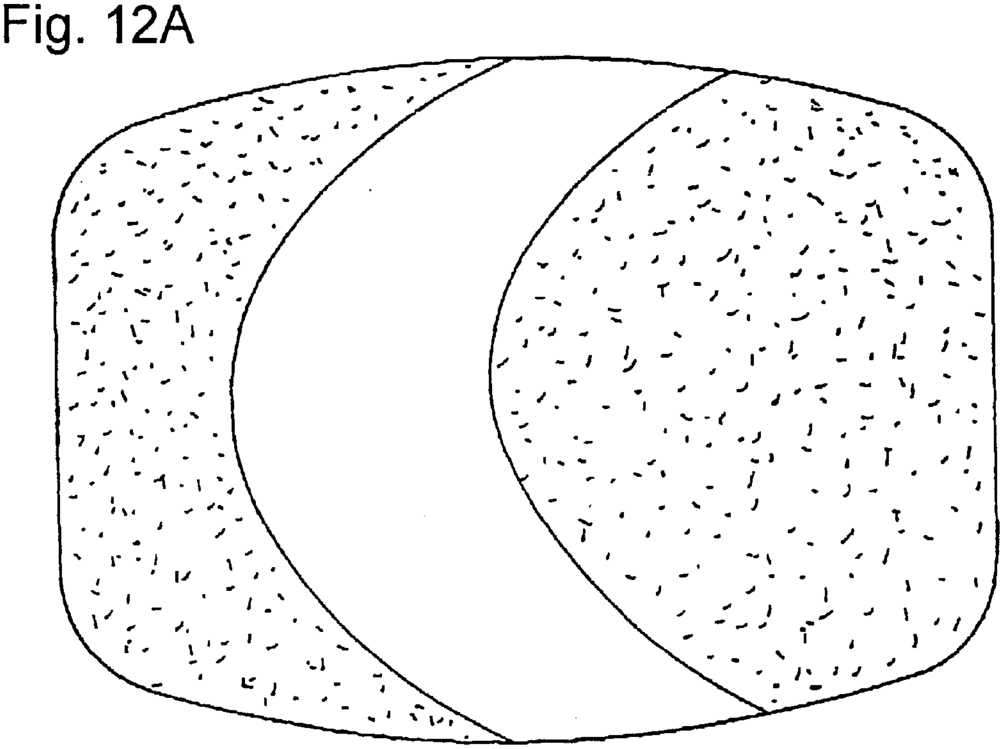
FIG. 12A shows a top view of a three-phase soap with a displaced section.
Figure 12B:
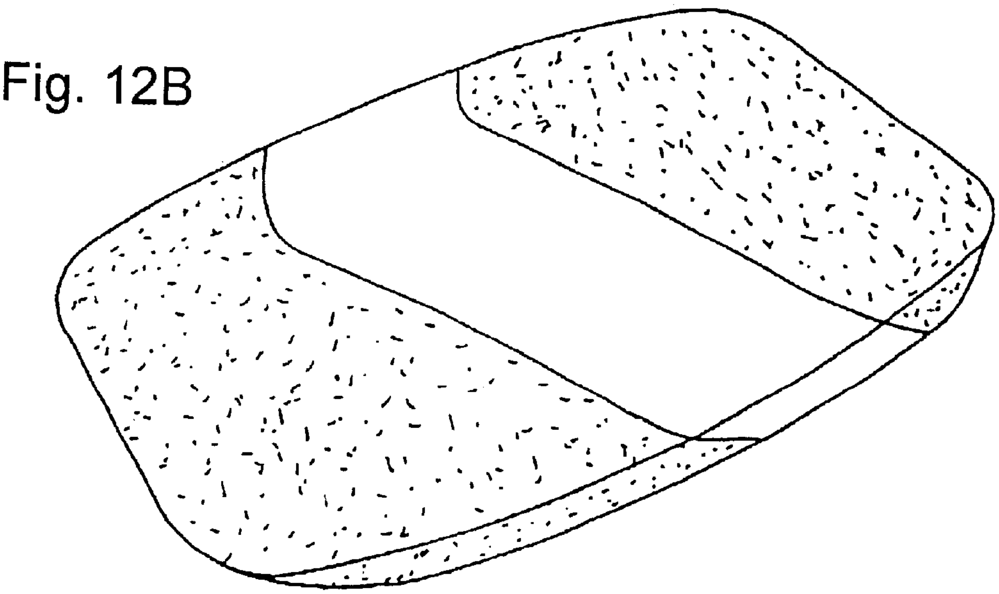
FIG. 12B shows a perspective view of the soap of FIG. 12A.

The mechanical durability of a soap is of importance for suitability during daily use. It is demonstrated that multiphase soaps with a diagonal section are more durable than would be expected on the basis of the sectional area and, in particular, more durable than soaps with a straight vertical cut (FIGS. 7A–7B, 8A–8B and 9A–9B). Using a device (FIG. 11), fracture experiments with weights were carried out on soaps having different types of design and different combinations of soap formulation. The device has a lever arm (5), which on one side has a plate (3) on which the weight may be placed to place strain on the soap (4). On the other side, the lever arm is pivotably mounted. The soap bar (4) is supported by a flexible holding device (6). The device loads the bar of soap (4) in the center in order to simulate stress in daily use, e.g., simple falling to the ground. The bars of soap were loaded in chronological order of ten seconds in each case with weights from five kg upwards in 0.5 kg steps. Provided a weight was held, the soap was loaded with a further weight until fracture of the soap occurred.

TABLE 1

Fracture stability

Figure 1B:
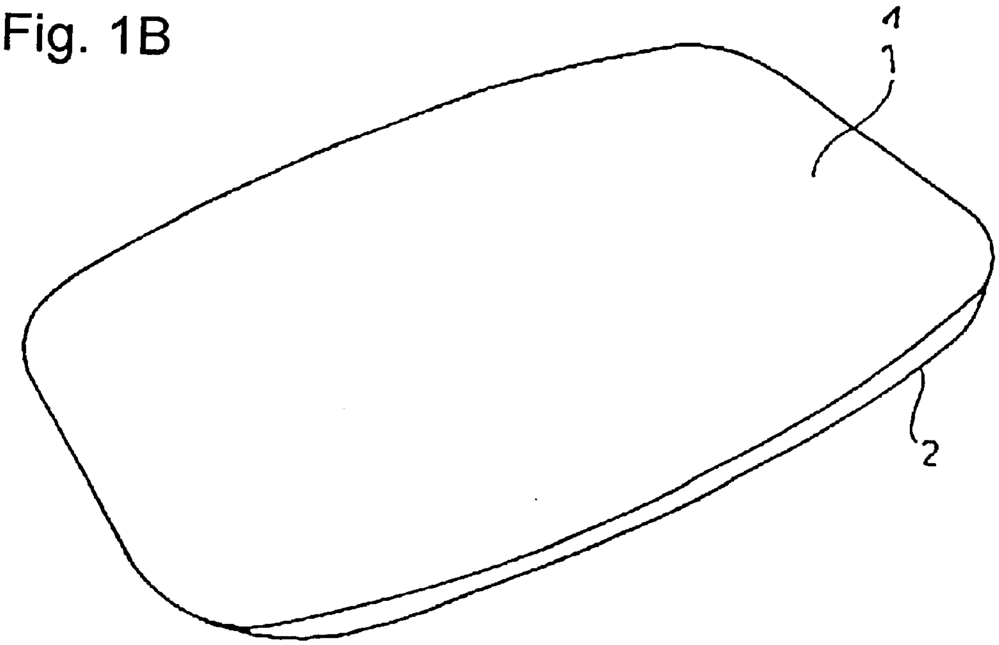
FIG. 1B shows a perspective view of the soap of FIG. 1A.
Figure 2A:
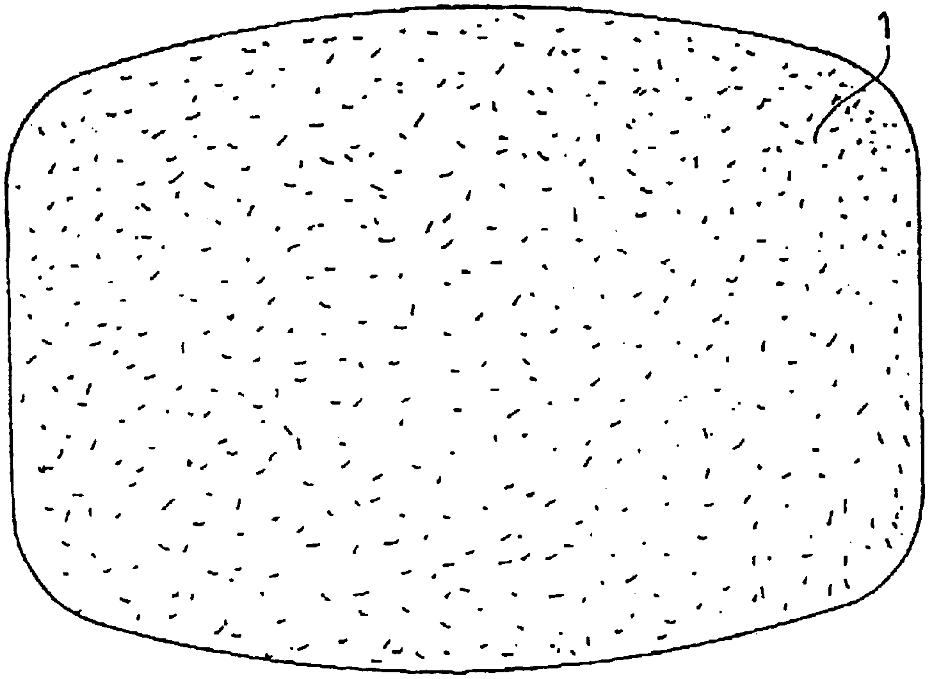
FIG. 2A shows a top view of a soap with horizontal soap layers according to DE-A 3 154 813
Figure 2B:
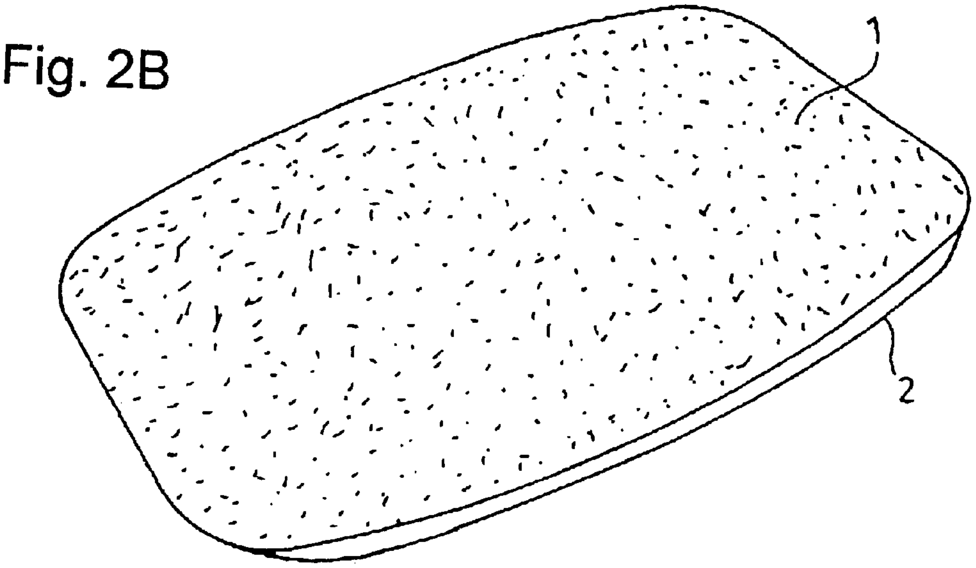
FIG. 2B shows a perspective view of the soap of FIG. 2A.
Figure 7A:
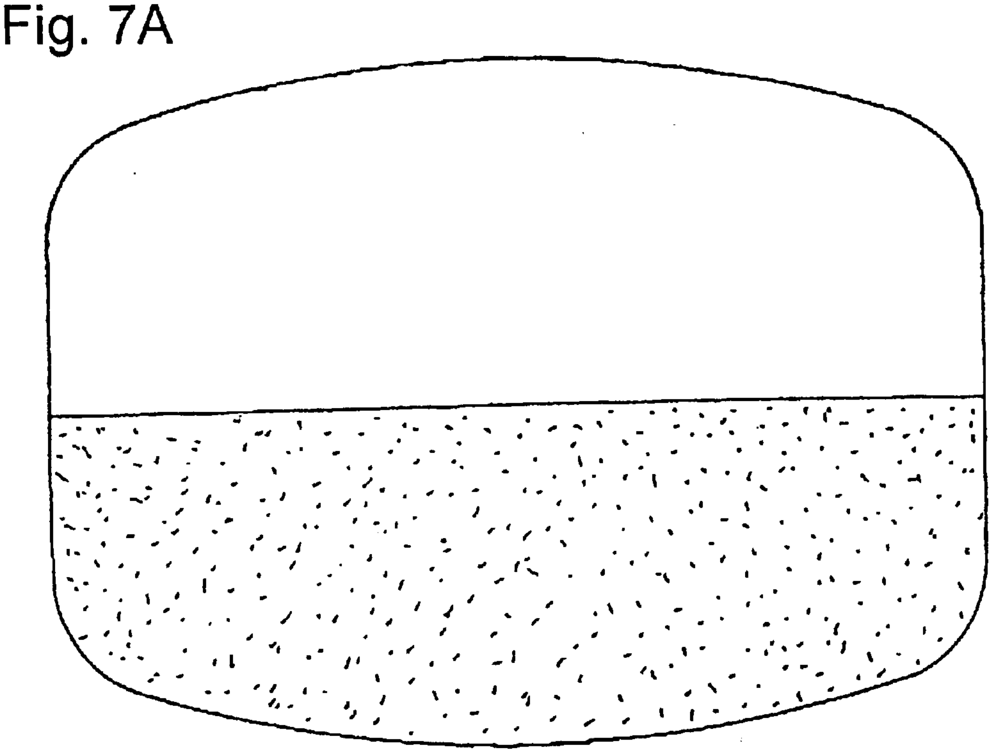
FIG. 7A shows a top view of a longitudinal section through a two-phase soap.
Figure 7B:
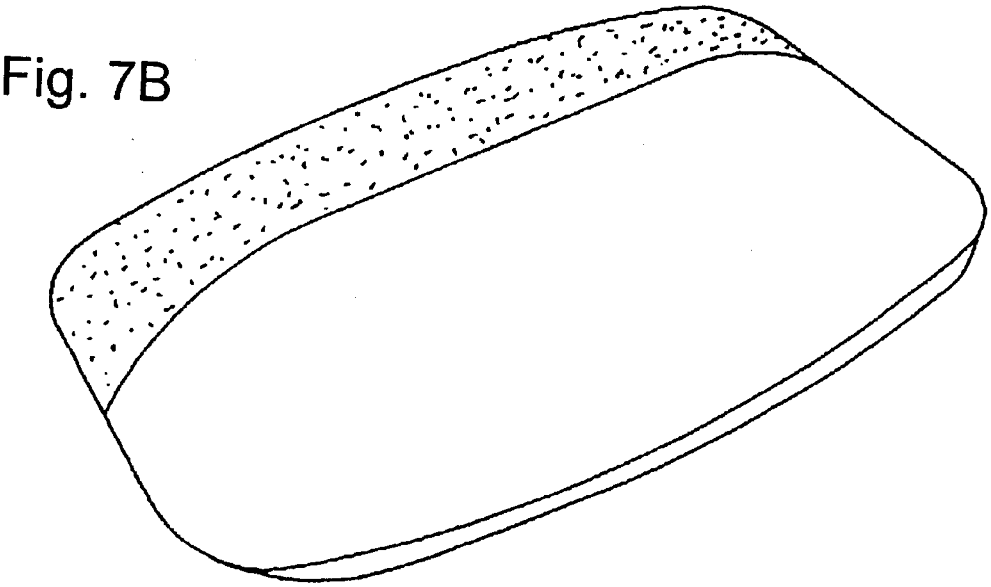
FIG. 7B shows a perspective view of the soap of FIG. 7A.
Figure 8A:
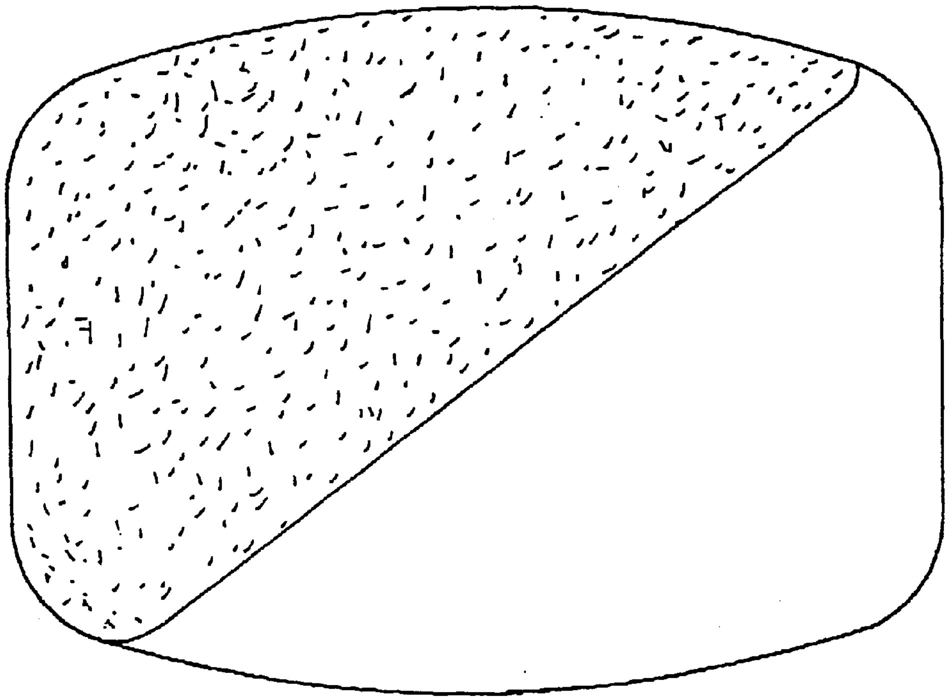
FIG. 8A shows a top view of a diagonal section of a two-phase soap
Figure 8B:
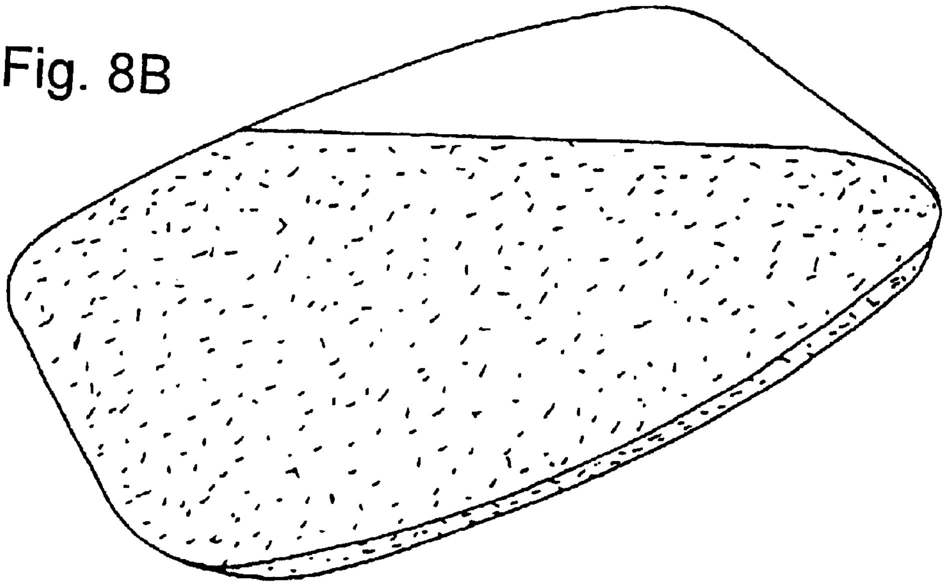
FIG. 8B shows a perspective view of a diagonal section of the soap of FIG. 8A.
Figure 9A:
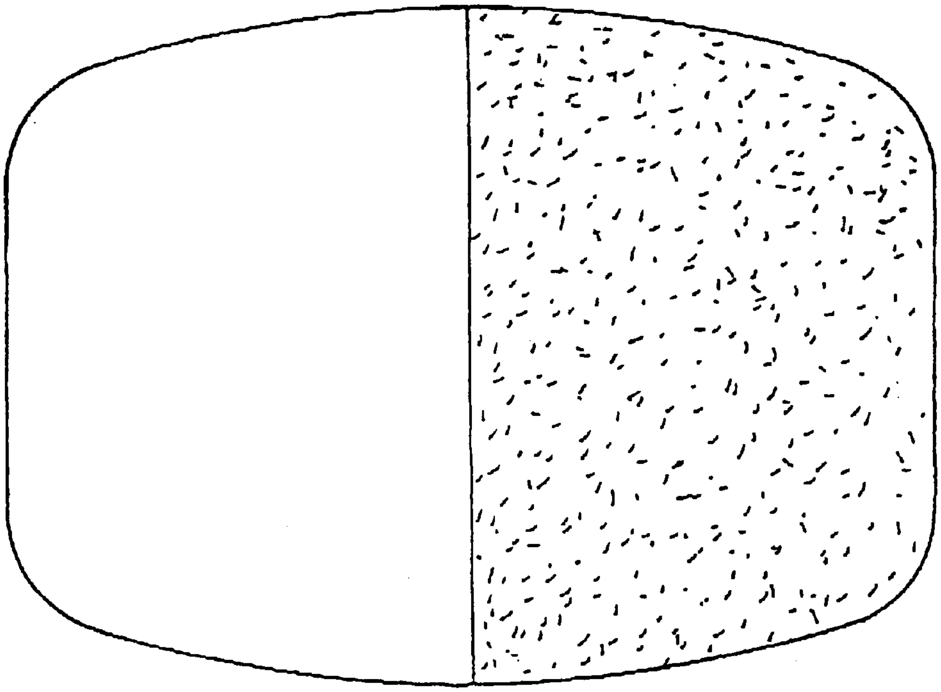
FIG. 9A shows a top view of a cross section of a two-phase soap.
Figure 9B:
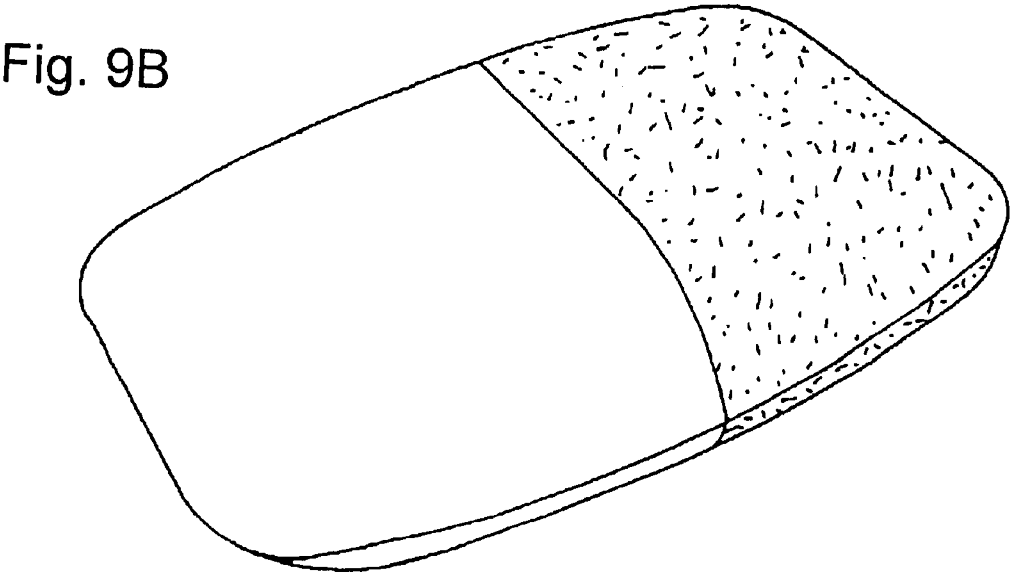
FIG. 9B shows a perspective view of a cross section of the soap of FIG. 9A.

| Type | Fracture weight [kg] | Standard deviation [kg] | Relative standard deviation [%] |
|---|---|---|---|
| T1 FIGS. 1A/1B | 20 | 1 | 5 |
| T2 FIGS. 9A 9B | 7.5 | 0.5 | 7 |
| T3 FIGS. 7A 7B | 9.5 | 0.5 | 5 |
| T4 FIGS. 2A 2B | 19.5 | 0.75 | 4 |
| T6 FIG. 8A 8B | 8.5 | 0.5 | 6 |
| T7 FIGS. 3A 3B /58° | 12.5 | 0.5 | 4 |
| T8 FIGS. 3A 3B /38° | 15.5 | 0.75 | 5 |
| T9 FIGS. 3A 3B /35° | 20.5 | 0.75 | 4 |

It can be seen that the types of soap with the diagonal design are significantly more loadable, and there is therefore considerably greater durability in daily use. The results of the fracture tests were confirmed by consumers during daily use.

2. Preference Test with Regard to Design

Consumer preference was carried out in a comparison test with the three soap types of horizontal section (FIGS. 2A and 2B), vertical section (FIGS. 9A and 9B) and the diagonal section according to the present invention (FIGS. 3A and 3B). Of the 100 people questioned, three of those questioned preferred the vertical sectional type, four of those questioned preferred the horizontal sectional type and 93 of those questioned preferred the novel diagonal sectional type. This means that the novel design was chosen with a significance of >99.9%.

Because of the novelty of the harmonious combination of two soap phases, there is interest in an application.

3. Preference Test With Regard to Scent

Consumer preference for scent was carried out in a comparison test with two two-phase soap bars: a two-phase soap bar A (equal proportions by area, diagonal section through the central point, FIGS. 3A and 3B) with two different perfumings was compared against another soap bar B of identical construction which had been perfumed with a 1:1 mixture of these two compositions. The perfume concentration was 1% in both bars of soap.

It was found that the scent is more intensive in the soap bar with the separate perfume oils A. Both perfume oils were perceived in parallel. The scent gains an additional dimension.

4. Formulation

In addition to the perfume oil, soaps also comprise active ingredients, such as cooling substances, UV filters, antibacterial active ingredients, deodorizing active ingredients and others. These active ingredients are frequently expensive and are therefore only incorporated into soaps in small amounts. The concentration of the individual active ingredients is often below the limit of effectiveness. In the novel two- or multiphase soap it is possible to incorporate such an active ingredient in a targeted manner into one of the soap phases. As a result of the concentration of active ingredients in one part of the soap, increased effectiveness is achieved in the case of targeted application of one soap phase.

5. Recognition Tests

To achieve a visible effect in a case of a multiphase soap, it must be possible to distinguish a certain proportion of the two phases when the soap viewed from above or from a customary viewing angle of about 45°. Three tests for the spontaneous recognition of multiphase soaps are described below.

The first soap phase is defined as the soap phase with the largest visible portion based on the area of soap projected in top view. The second soap phase is the soap phase with the second largest visible proportion. The visible proportion of the second and subsequent soap phases is expressed as a ratio of the projected area of the soap relative to the first soap phase or as a percentage of the overall area.

Tests for soaps having the new diagonal type: to determine the spontaneous recognition effect of multiphase soaps, six different test groups each of 20 participants were shown the bar of soap to be assessed (color combination green/white, FIGS. 3A and 3B) for three seconds viewed from above from a distance of one meter. The participants were then asked about what they had seen and the number of different soap phases. In these consumer-oriented tests, it was found that a very good recognition effect exists for the diagonal soap type (transverse type second phase at one end) if, in top view, the area ratio of first to second soap phase is about 5.6:1 or if the proportion of the second soap phase of the overall area is about 15%. Below a proportion of 10%, the spontaneous recognition decreases significantly (see Table "recognition rate of multiphase soaps experiment 2"). A poor recognition effect is found if a two-phase bar of soap with the horizontal design (FIGS. 2A and 2B, color combination green-white) is viewed from a viewing angle of about 450. In the case of this type of two-phase soap, no recognition of the two phases is possible when viewed directly from above. At a viewing angle of 450 a ratio of 1:12.5 or about 8% of the visible area for the second soap phase likewise arises.

TABLE 2

Recognition of two or more phases of a soap (FIGS. 3A and 3B diagonal type according to the present invention) as a function of the area ratios of the individual soap phase in top view.

| Second to first phase area ratio | Second phase area percent of overall area | Phases recognized | Phases not recognized |
|---|---|---|---|
| 1:20 | 5 | 4 | 16 |
| 1:10 | 10 | 8 | 12 |
| 1:6.7 | 15 | 16 | 4 |
| 1:5 | 20 | 18 | 2 |
| 1:4 | 25 | 20 | 0 |
| 1:3.3 | 30 | 20 | 0 |

Formulation Section for Different Types of Soap:

For the preparation of multiphase soaps it is possible to use, as soap bases, e.g., alkali metal soaps, syndets or combinations of the two. In the case of all combinations of the soap bases, the water content of the individual soap formulations is to be taken into consideration. Because of the varying shrinkage of the individual soap formulations, separation at the contact surface and thus breaking of the soap may arise. By suitably adjusting the water content in the individual soap formulations and by virtue of the new diagonal design it is possible to use numerous combinations of soap combinations for the preparation of stable multiphase soaps.

Since the so-called solid skin-cleansing composition can, by virtue of different additives and a special preparation process, also be prepared in transparent or opaque form, it is possible to prepare a very wide variety of combinations, including, of course, colored ones.

Using the multiphase soaps, scent accords can be represented which would lead to discolorations in purely white soaps. During the preparation of multiphase soaps, the perfume oil constituents which may lead to discolorations are taken up in the colored part. Perfume oil constituents which tend toward clouding in transparent soap are taken up in the opaque or nontransparent phase.

Preparation Process:

The preparation of soaps is known (Soaps and Detergents, Luis Spitz, 0-935315-72-1 and Production of Soap, D. Osteroth, 3-921956-55-2). The preparation of the novel multiphase soaps was carried out as described in the process below as example: first, the soap bases are admixed with the above-described additives, such as perfume oil, cosmetic ingredients, dyes, stabilizers and further additives, and then milled. The soap composition was then extruded at a jacket temperature of about 22° C. and a head temperature of about 45° C.

The resulting soap strands are then cut to the soap shape. The same is carried out for the soap strands of the second soap phase. The two soap strands are then cut in parallel and diagonally corresponding to the subsequent cutting shape and design type at an angle of from 140 to 70°. Prior to the stamping operation, the soap strands prepared in this way are aligned by means of the soap mold. The stamping operation was carried out, depending on the type of soap stamping machine used, with a pressing weight of from about 1.0 to 2.0 t or a pressing force of from 4 to 10 bar. During this stamping operation, both soap compositions have a temperature of from about 40 to 50° C.

Reference Number List

In FIGS. 2–4,

Ref No.

1. Phase 1.

2. Phase 2.

In FIG. 10,

3. Leverarm

4. Plate

5. Weights for loading onto the soap

6. Rotatable mounting of the lever arm

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A soap comprising two or more phases, wherein said two or more phases are visible when viewed from above and from the side, wherein said two or more phases are diagonally cut, wherein the individual phase is cut at an angle of 14° to 70°, and wherein the points of intersection of said phases are joined under pressure so that cambering arises at said points of intersection.

2. A soap according to claim 1, wherein each phase is visible in the vertical, longitudinal and transverse projection to at least 15% based on the overall projected area.

3. A soap according to claim 1, wherein each phase is visible in the vertical, longitudinal and transverse projection to at least 20% based on the overall projected area.

4. A soap according to claim 1, wherein the areas of the adjacent phases are cut diagonally and cambered towards one another.

5. A soap according to claim 1, wherein each phase comprises different perfume oils, cosmetic ingredients, active ingredients, dyes and/or further additives.

6. A process for the preparation of multiphase soap comprising two or more phases, wherein said two or more phases are visible when viewed from above and from the side, comprising the step of diagonally cutting in the form of soap strands the individual phases at an angle of from 14° to 70°, and the points of intersection are joined under pressure so that cambering arises at the points of intersection.

7. A process according to claim 6, wherein the angle is 30° to 55°, and the points of intersection are joined under pressure so that cambering arises at the points of intersection.

* * * * *